US012746248B2

(12) United States Patent
Mousa

(10) Patent No.: US 12,746,248 B2
(45) Date of Patent: Sep. 29, 2026

(54) COMPOUNDS AND FORMULATIONS

(71) Applicant: PRO-AL MEDICO-TECHNOLOGIES, INC., Suffern, NY (US)

(72) Inventor: Shaker A. Mousa, Wynantskill, NY (US)

(73) Assignee: PRO-AL MEDICO-TECHNOLOGIES, INC., Suffern, NY (US)

( * ) Notice: Subject to any disclaimer, the term of this patent is extended or adjusted under 35 U.S.C. 154(b) by 1120 days.

(21) Appl. No.: 17/775,713

(22) PCT Filed: Nov. 10, 2020

(86) PCT No.: PCT/US2020/059882
§ 371 (c)(1),
(2) Date: May 10, 2022

(87) PCT Pub. No.: WO2021/092597
PCT Pub. Date: May 14, 2021

(65) Prior Publication Data

US 2023/0018014 A1 Jan. 19, 2023

Related U.S. Application Data

(60) Provisional application No. 62/933,504, filed on Nov. 10, 2019.

(51) Int. Cl.
*A61K 31/664* (2006.01)
*A61K 9/51* (2006.01)
(Continued)

(52) U.S. Cl.
CPC .......... *A61K 31/664* (2013.01); *A61K 9/5153* (2013.01); *A61K 9/5161* (2013.01);
(Continued)

(58) Field of Classification Search
CPC .. A61K 31/664; A61K 9/5153; A61K 9/5161; A61K 31/198; A61K 45/06; A61P 9/00; A61P 25/00; B82Y 5/00
See application file for complete search history.

(56) References Cited

U.S. PATENT DOCUMENTS

| | | |
|---|---|---|
| 5,998,457 A | 12/1999 | Kaddurah-Daouk |
| 6,075,031 A | 6/2000 | Kaddurah-Daouk et al. |

(Continued)

FOREIGN PATENT DOCUMENTS

| | | |
|---|---|---|
| WO | 1998022479 A1 | 5/1998 |
| WO | WO 1999/043307 A1 | 9/1999 |

(Continued)

OTHER PUBLICATIONS

Liang et al., "Myocardial Protection by Phosphocreatine in Extracorporeal Circulation Surgery for Ventricular Septal Defects Combined with Pulmonary Hypertension in Infants and Young Children," Chinese Remedies & Clinics, vol. 17, No. 7, p. 1010-1012, (2017), English Machine Translation.

(Continued)

*Primary Examiner* — Clinton A Brooks
*Assistant Examiner* — Kendall Nicole Heitmeier
(74) *Attorney, Agent, or Firm* — Hoxie & Associates LLC

(57) ABSTRACT

This disclosure presents compositions comprising phosphocreatine and nanoparticles containing triiodothyronine (T3), and to their use in treatment of cardiac conditions, particularly cardiac arrest and acute heart failure, as well as conditions generally relating to hypoxia, such as ischemia and stroke.

11 Claims, 19 Drawing Sheets

(51) Int. Cl.

| | |
|---|---|
| ***A61K 31/198*** | (2006.01) |
| ***A61K 45/06*** | (2006.01) |
| ***A61P 9/00*** | (2006.01) |
| ***A61P 25/00*** | (2006.01) |
| *B82Y 5/00* | (2011.01) |

(52) U.S. Cl.

CPC ............ *A61K 31/198* (2013.01); *A61K 45/06* (2013.01); *A61P 9/00* (2018.01); *A61P 25/00* (2018.01); *B82Y 5/00* (2013.01)

(56) References Cited

U.S. PATENT DOCUMENTS

| | | | | |
|---|---|---|---|---|
| 2010/0086596 | A1 * | 4/2010 | Thanoo ................ | A61K 9/0019 424/486 |
| 2010/0094120 | A1 | 4/2010 | Renshaw | |
| 2012/0315320 | A1 | 12/2012 | Davis et al. | |
| 2013/0243868 | A1 | 9/2013 | Rubin et al. | |
| 2014/0044690 | A1 | 2/2014 | Chen et al. | |

FOREIGN PATENT DOCUMENTS

| | | | | |
|---|---|---|---|---|
| WO | WO-2012170017 | A1 * | 12/2012 | ......... A61K 47/6939 |
| WO | WO 2015/079404 | A1 | 6/2015 | |
| WO | WO-2019180199 | A1 * | 9/2019 | .............. C07F 9/222 |

OTHER PUBLICATIONS

CN101732263, Jun Yang, “Creatine phosphate sodium freeze-dried preparation and preparation method thereof” English language translation.

Zheng et al., “3'-Iodothyronamine: A New Weapon To Protect The Heart And Regulate Metabolism”, *Int. J. Endocrinol. Metab.*, 39(2), (2019). English Abstract Only.

Karakus et al., “Development of Triiodothyronine Polymeric Nanoparticles for Targeted Delivery in the Cardioprotection against Ischemic Insult”, *Biomedicines*, 9(11), 1713, (2021).

Weil et al., “Preclinical Evaluation Of Triiodothyronine Nanoparticles As A Novel Therapeutic Intervention For Resuscitation From Cardiac Arrest”, Resuscitation, vol. 186, 109735, (2023).

Mdzinarishvili et al., “Engineering Triiodothyronine (T3) Nanoparticle for Use in Ischemic Brain Stroke,” Drug Deliv and Transl Res., vol. 3, 10 pages, (2013).

Chen et al., “Short Term Triiodo-L-thyronine Treatment Inhibits Cardiac Myocyte Apoptosis in Border Area After Myocardial Infarction in Rats,” J Mol Cell Cardiol., vol. 44, No. 1, 17 pages, (2008).

Landoni et al., “Cardiac Protection with Phosphocreatine: A Meta-analysis,” Interactive CardioVascular and Thoracic Surgery, vol. 23, p. 637-647, (2016).

Li et al., “Neuroprotective Effect of Phosphocreatine on Oxidative Stress and Mitochondrial Dysfunction Induced Apoptosis In Vitro and In Vivo: Involvement of Dual PI3K/Akt and Nrf2/HO-1 Pathways,” Free Radic Biol Med., vol. 120, p. 228-238, (2018); English Abstract Only.

Mdzinarishvili et al, “Engineering Triiodothyronine (T3) Nanoparticie for Use in Ischemic Brain Stroke,” Drug Deliv and Transl Res., vol. 3, 10 pages, (2013).

Yan et al., “Effect of Exogenous Phosphocreatine on Cardiomycytic Apoptosis and Expression of Bcl-2 and Bax After Cardiopulmonary Resuscitation in Rats,” World J Emerg Med., vol. 2, No. 4, 6 pages, (2011).

* cited by examiner

COMPOUNDS AND FORMULATIONS

CROSS-REFERENCE TO RELATED APPLICATIONS

This application is a U.S. National Stage Application under 35 U.S.C. § 371 claiming benefit of PCT Application No. PCT/US2020/059882, filed on Nov. 10, 2020, which claims priority to and the benefit of U.S. Provisional Application Ser. No. 62/933,504, filed on Nov. 10, 2019, the contents of each of which are hereby incorporated by reference in its entirety.

TECHNICAL FIELD

The field relates to compositions comprising phosphocreatine and nanoparticles containing triiodothyronine (T3), and to their use in treatment of cardiac conditions, particularly cardiac arrest and acute heart failure, as well as conditions generally relating to hypoxia, such as ischemia and stroke, neurological disorders, and disorders characterized by low cellular energy (e.g., disorders characterized by mitochondrial dysfunction).

BACKGROUND OF THE INVENTION

Cardiac arrest refers to a state where the heart of the patient has stopped beating effectively and is no longer functioning to pump blood around the body. It is often caused by myocardial infarction. If treated promptly, cardiac arrest may sometimes be reversed by cardiopulmonary resuscitation (CPR) and defibrillation. Drugs to treat cardiac arrest include epinephrine, which stimulates the heart muscle and also augments pressure in the aorta, which drives coronary perfusion. Whether epinephrine significantly improves overall survival is controversial, however, because while it may improve the chances for resuscitation, it may also cause arrhythmias and strain on the heart which increase the risk of problems in the post-resuscitation phase.

Other forms of acute cardiac insufficiency include acute heart failure and cardiogenic shock. Acute heart failure is a critical condition that is commonly seen in patients with chronic heart disease. During acute heart failure, the ability of the heart to pump blood from the lung circulation into the peripheral circulation is impaired. Cardiogenic shock is a form of shock resulting from an inadequate circulation of blood due to primary failure of the ventricles of the heart to function effectively.

Triiodothyronine, also known as T3, is a thyroid hormone. Thyroid-stimulating hormone (TSH) activates the production of thyroxine (T4) and T3. T4 is converted to T3 by deiodination. T3 affects a variety of body processes, including body temperature, growth, and heart rate. T3 has important effects on cardiac tissue. Thyroid hormones, notably T3, modulate ventricular function via genomic and non-genomic mechanisms. Cardiac stress events (cardiac arrest, myocardial infarction, etc.) are associated with steep reductions in serum T3 levels. Post resuscitation T3 level correlates highly with survival rate. T3 additionally has cardiostimulatory properties: it increases the cardiac output by increasing the heart rate and force of contraction. Overall, there is reason to believe that early bolus T3 injection could increase chances of resuscitating cardiac arrest victims, and that elevating T3 serum concentration could increase prospects of survival to hospital discharge.

Cardioprotection is a key purpose of the therapeutic interventions in cardiology, which aim to reduce infarct size and thus prevent progression toward heart failure after acute ischemic and cardiac arrest events. Recent studies have highlighted the role of the thyroid system in cardioprotection, particularly through the preservation of mitochondrial function, its anti-fibrotic, and pro-angiogenetic effects, cell membrane repolarization, and the induction of cell regeneration. Triiodothyronine/thyroxine (T3) therapy has been used to reverse myocardial stunning. Hyperthyroidism prevents the stunning with high dependence on the mitochondrial sodium-calcium exchanger and mitochondrial K+ channels.

The heart is incapable of storing significant oxygen and thus is dependent on a continuous delivery of flow in order to support its high metabolic state. Following cardiac arrest, myocardial tissue oxygen tension falls rapidly and aerobic production of ATP ceases. Generally, without re-oxygenation of the ischemic myocardium, return of spontaneous circulation (ROSC) cannot be achieved. Epinephrine is currently used to induce the return of ROSC. However, the use of epinephrine has come under scrutiny for causing various negative side effects, such as hypertension and pulmonary edema. In addition, it has not been shown to improve long-term survival or mental function after recovery.

It is therefore desirable to create a treatment that could restore ROSC without the potential side effects of epinephrine.

SUMMARY OF THE INVENTION

Phosphocreatine, hereinafter alternatively referred to PCR, is a phosphorylated creatine molecule that serves as a rapidly mobilizable reserve of high-energy phosphates in skeletal muscle and the brain to recycle adenosine triphosphate, the energy currency of the cell. Phosphocreatine is capable of anaerobically donating a phosphate group to ADP to form ATP. Use of phosphocreatine for quick regeneration of ATP during intense activity can provide a spatial and temporal buffer of ATP concentration.

The inventors have surprisingly found that nanoparticles of T3 and phosphocreatine restore ATP levels in cardiac myocytes under hypoxic conditions. It is believed that this novel combination could provide a treatment that could restore ROSC without the potential side effects of epinephrine. This combination of T3 phosphocreatine in nanoparticle form represents a potentially new therapeutic for the control of tissue damage in cardiac ischemia and resuscitation. The inventors have also surprisingly found that the compositions of the present disclosure are capable of crossing the blood brain barrier, which implies that the nanoparticles of T3 and phosphocreatine could also be used to treat various disorders related to hypoxia in the brain. The results strongly suggest further applications in conditions characterized by low cellular energy, including conditions related to hypoxia.

In one aspect, the present invention provides for nanoparticles encapsulating both T3 and PCR wherein the nanoparticle comprises chitosan and PLGA, wherein the relative ratio of chitosan to PLGA may be altered to adjust the release of the active ingredients, e.g. T3 and/or PCR. Without being bound by theory, it is believed that chitosan is hydrophilic. Therefore, where the active ingredient may possibly be hydrophobic (e.g. T3 and PCR) the addition of more chitosan relative to PLGA may result in a nanoparticle wherein the active ingredient is quickly released upon application or administration, e.g., a relative ratio amount of 80/20, (e.g., % w/w 80/20, chitosan to PLGA) chitosan to PLGA, or a relative ratio amount of 90/10 (e.g., % w/w 90/10, chitosan to PLGA) chitosan to PLGA. Without being bound by theory, where the active ingredient is more hydrophobic, the addition of more PLGA, relative to the amount of chitosan, may result in a nanoparticle wherein the active ingredient is more slowly released, e.g., a relative ratio of 20/80 chitosan to PLGA (e.g., % w/w 20/80, chitosan to PLGA), or 10/90 chitosan to PLGA (e.g., % w/w 10/90, chitosan to PLGA).

In a further embodiment, the present disclosure provides for a method for the prophylaxis or treatment of a disease, disorder or condition characterized by a deficiency of adenosine triphosphate (ATP), comprising administration of a therapeutically effective amount of triiodothyronine (T3) and phosphocreatine (PCR) to a subject in need thereof. In various embodiments, the disease, disorder or condition is selected from a cardiovascular disorder, a disorder relating to hypoxia, or a disorder characterized by low cellular energy (e.g., disorders characterized by mitochondrial dysfunction or disorders characterized by dysfunction of ATP synthase), a neurodegenerative disorder, a respiratory disorder, obesity, a metabolic disorder, or diabetes mellitus In one embodiment, the present disclosure provides a method for treating a cardiac condition, e.g. cardiac arrest, cardiac arrhythmia, cardiac insufficiency, myocardial infarction, myocardial ischemia/reperfusion injury, myocardial infarction, myocardial hypoxia, or congestive heart failure, comprising administering a composition comprising effective amount of nanoparticles of T3 and phosphocreatine (PCR), to a patient in need thereof, wherein the composition comprises a bioabsorbable polymer, for example as described above.

In another embodiment, the present disclosure also provides a method for treating a disease or condition related to hypoxia, ischemia or ischemia-reperfusion injury, e.g., myocardial hypoxia, stroke (e.g., ischemic stroke or hemorrhagic stroke), traumatic brain injury (e.g., concussion), ischemia (e.g. myocardial ischemia or retinal ischemia), hemorrhagic shock, or edema (e.g., cerebral edema), comprising administering a composition comprising effective amount of a T3 nanoparticles and phosphocreatine (PCR), e.g., having the characteristics of any of the foregoing Composition 1 or 1.1-1.16, to a patient in need thereof, wherein the composition comprises a bioabsorbable polymer, for example as described above.

In a specific example of the methods disclosed herein, the nanoparticle administered comprises a chitosan-PLGA nanoparticles encapsulating T3 and PCR.

In yet another example, the nanoparticle administered includes chitosan-PLGA nanoparticles immobilizing both T3 and PCR. Alternatively, the nanoparticles administered comprises chitosan-PLGA nanoparticles immobilizing T3 and PCR as well as chitosan-PLGA nanoparticles encapsulating T3 and PCR.

DETAILED DESCRIPTION

Figure 1:
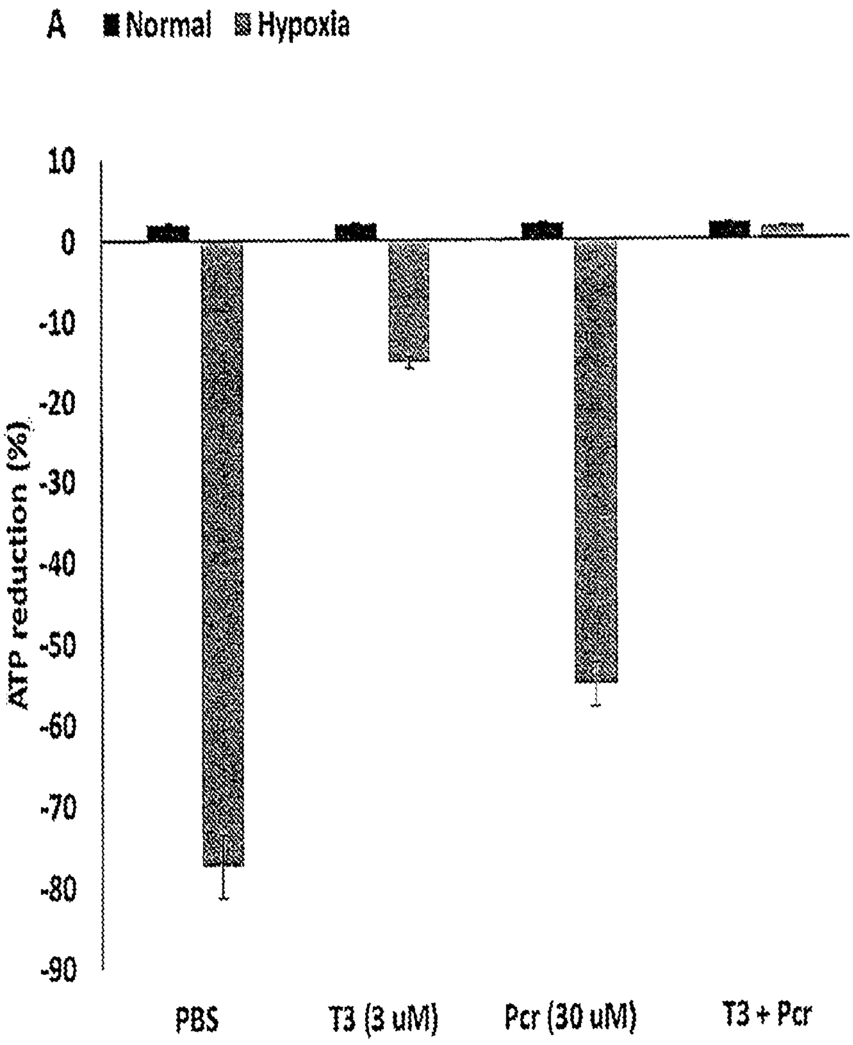
FIG. 1 depicts the effect the combination of T3 nanoparticles and PCR had on ATP levels in neonatal cardiac myocytes compared to controls.
Figure 2:
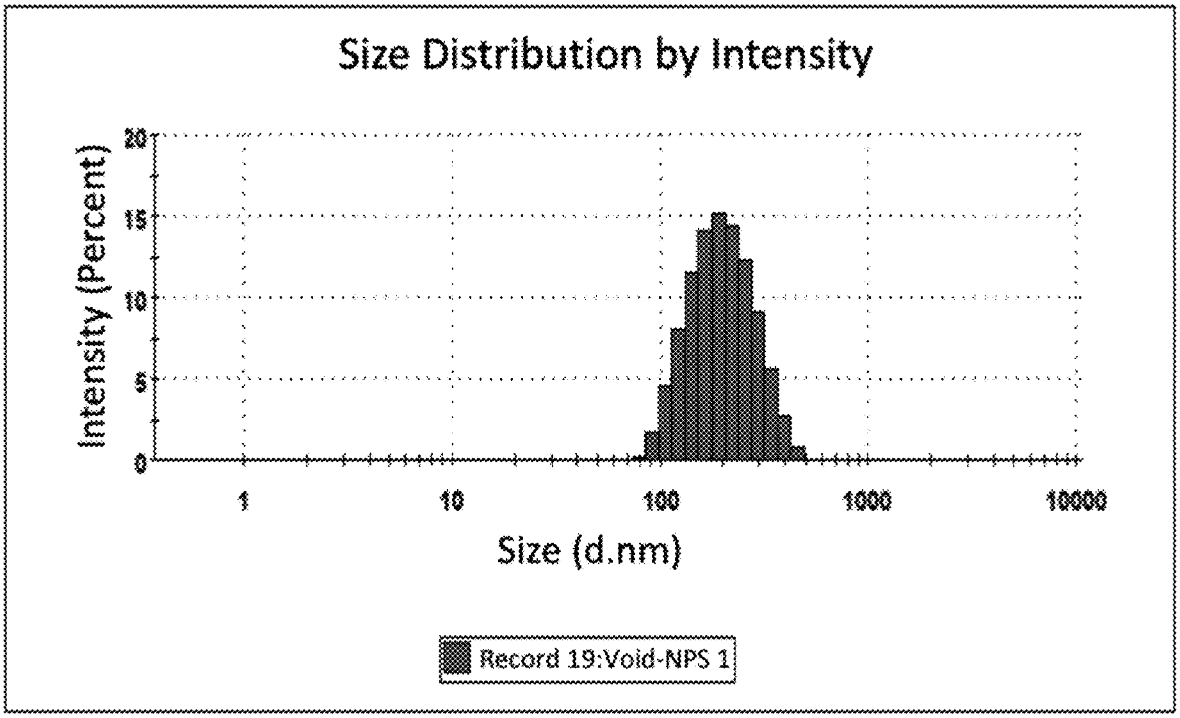
FIG. 2 depicts the particle size distribution of PLGA nanoparticles.
Figure 3:
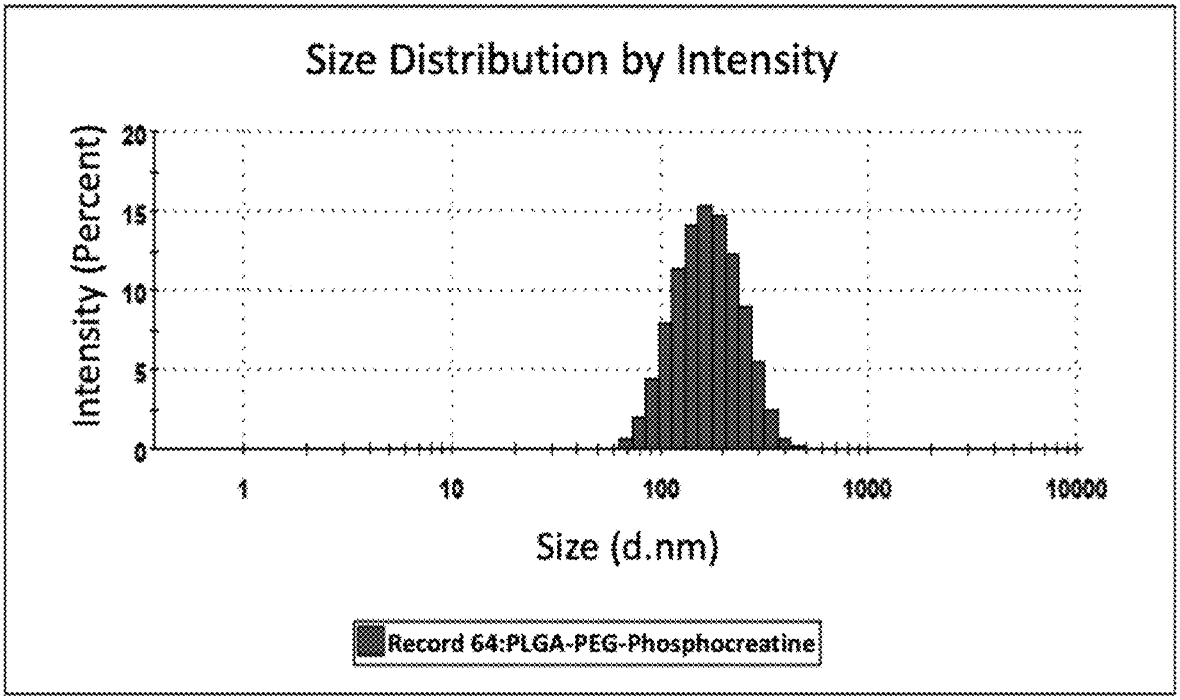
FIG. 3 depicts the particle size distribution of PLGA-PEG nanoparticles encapsulating phosphocreatine.
Figure 4:
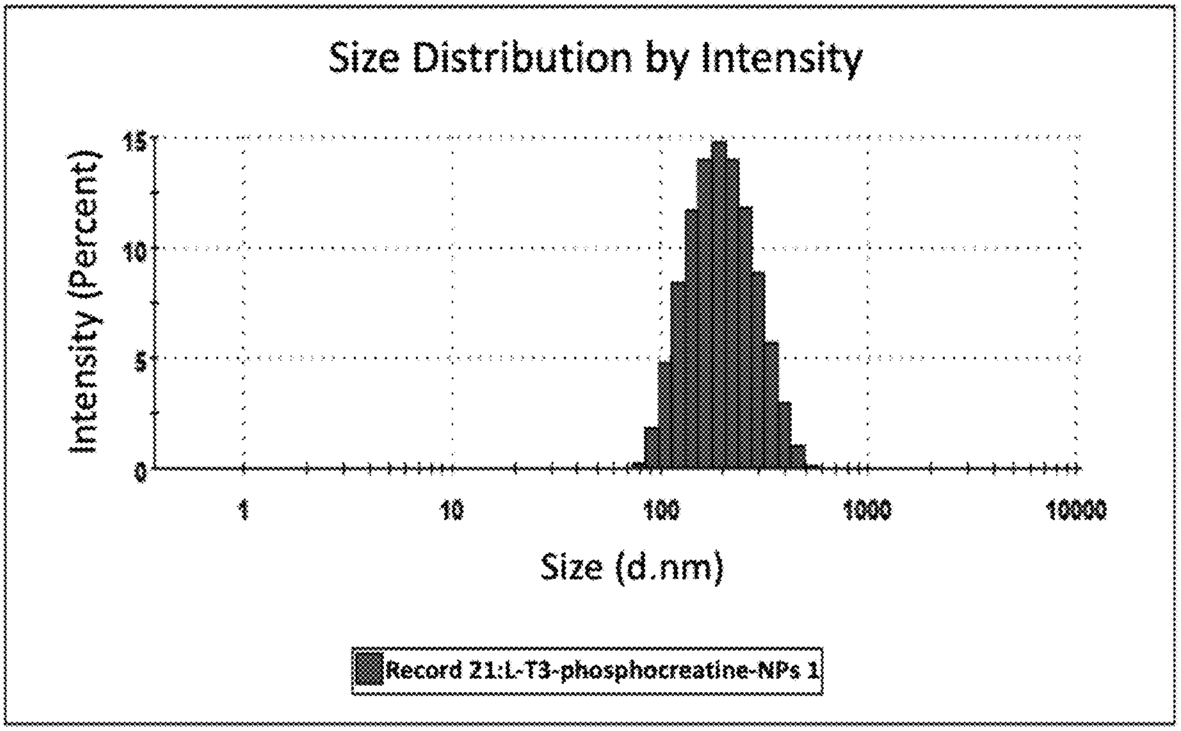
FIG. 4 depicts the particle size distribution of T3-PLGA nanoparticles encapsulating phosphocreatine.
Figure 5:
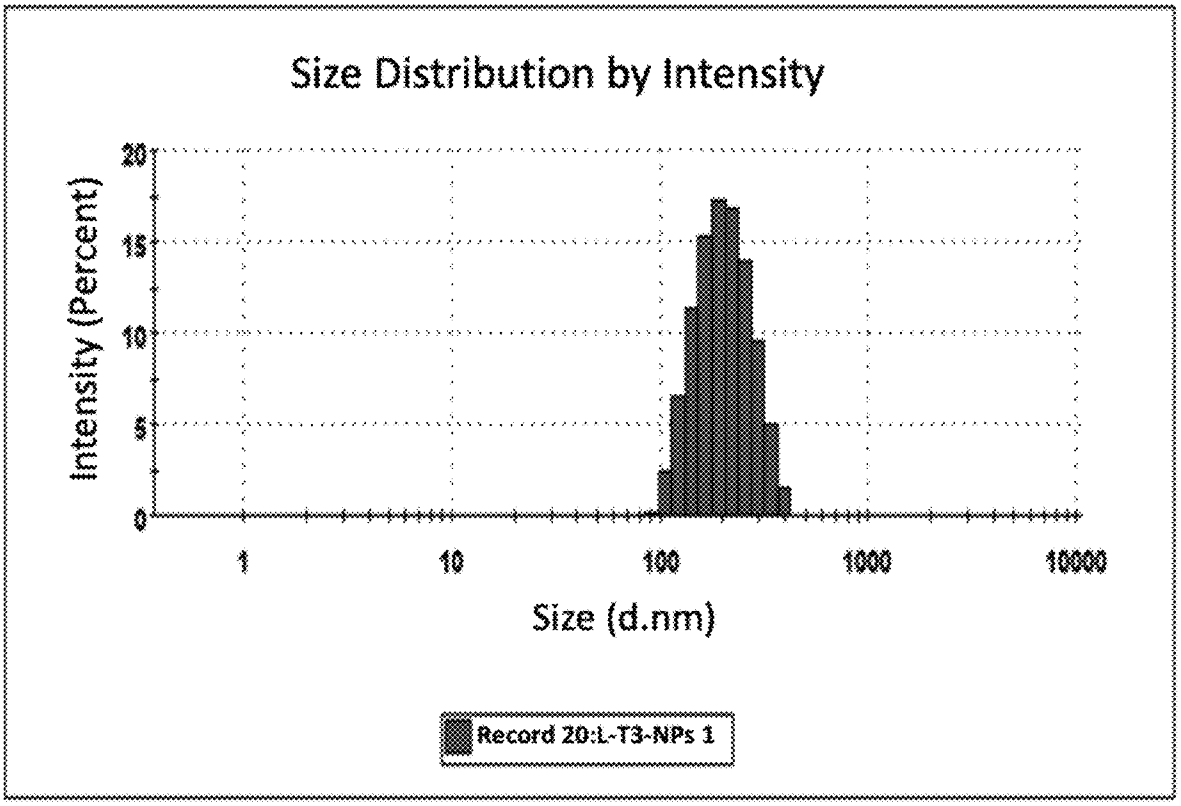
FIG. 5 depicts the particle size distribution of T3-PLGA nanoparticles.

The examples and drawings provided in the detailed description are merely examples, which should not be used to limit the scope of the claims in any claim construction or interpretation.

Compositions and Related Methods

Therefore, in one aspect, the present disclosure provides a composition (Composition 1) comprising nanoparticles of T3 and phosphocreatine (PCR) encapsulated or immobilized by a bioabsorbable polymer.

For example, Composition 1 may additionally have any of the following characteristics:

1.1 Composition 1, wherein the nanoparticles comprise the T3 (e.g., L-T3) conjugated by covalent bonding to a biodegradable polymer and the phosphocreatine (PCR) encapsulated within the biodegradable polymer.

1.2 Any of the preceding compositions, wherein the polymer comprises poly (lactic-co-glycolic acid) (PLGA) or polylactic acid (PLA), e.g., PLGA having 50/50 co-polymerization of D,L-lactic acid and glycolic acid.

1.3 Any of the preceding compositions, wherein the polymer comprises poly (lactic-co-glycolic acid) (PLGA) or polylactic acid (PLA), e.g., PLGA having 50/50 co-polymerization of D,L-lactic acid and glycolic acid optionally conjugated with a short chain Polyethylene Glycol (PEG, Molecular weight 100-2,000 Dalton.

1.4 Any of the preceding compositions, wherein the T3 nanoparticles have an average diameter of about 50-1000 nm, e.g., 50-500.

1.5 Any of the preceding compositions, wherein the T3 nanoparticles have an average diameter of about 100-300 nm, e.g., 200 nm.

1.6 Any of the preceding compositions, wherein the T3 nanoparticles have a zeta potential of 0 to −20 mV.

1.7 Any of the preceding compositions, wherein the T3 nanoparticles have a zeta potential of 0 to +20 mV.

1.8 Any of the preceding compositions, wherein T3 is covalently linked to the bioabsorbable polymer.

1.9 Any of the preceding compositions, wherein the nanoparticle comprises a second pharmacologically active ingredient.

1.10 Any of the preceding compositions, wherein the PLGA has a molecular weight range of about 5,000-50,000 Dalton, preferably 6,000-8,000 Dalton.

1.11 Any of the preceding compositions, wherein the PLGA-conjugated to PEG molecular weight range of 5,000-20,000 Dalton, preferably 6,000-8,000 Dalton.

1.12 Any of the preceding compositions, wherein the PLGA-conjugated to PEG molecular weight range of about 6,000-8,000 Dalton.

1.13 Any of the preceding compositions, wherein the T3 is chemically conjugated to PLGA or PLGA-PEG for assembly of Nanoparticles.

1.14 Any of the preceding compositions, wherein the composition is dispersed in a physiological sterile medium.

1.15 Any of the preceding compositions, wherein the composition is dispersed in saline or dextrose.

1.16 Any of the preceding compositions, wherein the biodegradable polymer comprises chitosan.

In a further aspect, the present disclosure provides for a method [Method 1] for the prophylaxis or treatment of a disease, disorder or condition characterized by a deficiency of adenosine triphosphate (ATP), comprising administration of a therapeutically effective amount of triiodothyronine (T3) and phosphocreatine (PCR) to a subject in need thereof.

1.1 Method 1, wherein the disease, disorder or condition is selected from a cardiovascular disorder, a disorder relating to hypoxia, or a disorder characterized by low cellular energy (e.g., disorders characterized by mitochondrial dysfunction or disorders characterized by dysfunction of ATP synthase), a neurodegenerative disorder, a respiratory disorder, obesity, a metabolic disorder, or diabetes mellitus.

1.2 Any of the preceding methods, wherein the disease, disorder or condition is a cardiovascular disorder (e.g., atherosclerosis (e.g., coronary atherosclerosis), ischemia-reperfusion (I/R) injury, hypertension (e.g., essential hypertension, pulmonary hypertension, secondary hypertension, isolated systolic hypertension, hypertension associated with diabetes, hypertension associated with atherosclerosis, renovascular hypertension), diabetes, cardiac hypertrophy, myocardial ischemia, myocardial infarction, cardiac arrest, cardiomyopathy (e.g., infantile cardiomyopathy), cardiac insufficiency, cardiogenic shock, left ventricular hypertrabeculation syndrome, and heart failure (e.g., acute heart failure)).

1.3 Any of the preceding methods, wherein the disease, disorder or condition is a disorder relating to hypoxia (e.g., hemorrhagic shock, organ failure (e.g., organ failure consequent to ARDS, sepsis, septic shock, or hemorrhagic shock), hypoxia consequent to organ transplant, renal failure (e.g., chronic renal failure), cerebral edema, papillomas, spinal cord injuries, stroke (e.g., ischemic stroke or hemorrhagic stroke), ischemia or ischemia-reperfusion injury, traumatic brain injury (e.g., concussion), brain hypoxia, spinal cord injury, edema (e.g., cerebral edema), and anemia).

1.4 Any of the preceding methods, wherein the disease, disorder or condition is a disorder characterized by low cellular energy (e.g., disorders characterized by mitochondrial dysfunction, (e.g., mitochondrial myopathy, e.g., Kearns-Sayre syndrome; Leigh syndrome; mitochondrial DNA depletion syndrome; mitochondrial encephalomyopathy, lactic acidosis, and stroke-like episodes (MELAS); diabetes mellitus and deafness; maternally inherited deafness and diabetes; mitochondrial neurogastrointestinal encephalomyopathy; myoclonus epilepsy with ragged red fibers; neuropathy, ataxia, and retinitis pigmentosa (NARP); Pearson syndrome), a disorder characterized by dysfunction of ATP synthase (e.g., apical hypertrophic cardiomyopathy and neuropathy, ataxia, autism, Charcot-Marie-Tooth Syndrome, encephalopathy, epilepsy with brain pseudoatrophy, episodic weakness, hereditary spastic paraplegia, familial bilateral striatal necrosis, Leber hereditary optic neuropathy, mesial temporal lobe epilepsies with hippocampal sclerosis (MTLE-HS), motor neuron syndrome, periodic paralysis, schizophrenia, spinocerebellar ataxia, tetralogy of Fallot).

1.5 Any of the preceding methods, wherein the disease, disorder or condition is a neurodegenerative disorder (e.g., Huntington's disease, Alzheimer's disease, Parkinson's disease) or a disorder characterized by cell membrane repolarization.

1.6 Any of the preceding methods, wherein the disease, disorder or condition is a respiratory disorder (e.g., emphysema, acute lung injury (ALI), acute respiratory distress syndrome (ARDS), chronic obstructive pulmonary disease (COPD), respiratory arrest, and asthma).

1.7 Any of the preceding methods, wherein the disease, disorder or condition is diabetes mellitus or a disorder consequent to diabetes (e.g., diabetic ulcers, gangrene and diabetic retinopathy).

1.8 Any of the preceding methods, wherein the disease, disorder or condition is a metabolic disorder (e.g., metabolic syndrome).

1.9 Any of the preceding methods, wherein the disease, disorder or condition is obesity.

1.10 Any of the preceding methods, wherein the T3 and PCR are presented in the form of a nanoparticle, wherein the T3 and phosphocreatine (PCR) are encapsulated or immobilized by a bioabsorbable polymer.

1.11 Method 1.10, wherein the nanoparticles comprise the T3 (e.g., L-T3) conjugated by covalent bonding to a biodegradable polymer and the phosphocreatine (PCR) encapsulated within the biodegradable polymer.

1.12 Any of methods 1.10-1.11, wherein the polymer comprises poly (lactic-co-glycolic acid) (PLGA) or polylactic acid (PLA), e.g., PLGA having 50/50 co-polymerization of D,L-lactic acid and glycolic acid.

1.13 Any of methods 1.10-1.12, wherein the polymer comprises poly (lactic-co-glycolic acid) (PLGA) or polylactic acid (PLA), e.g., PLGA having 50/50 co-polymerization of D,L-lactic acid and glycolic acid optionally conjugated with a short chain Polyethylene Glycol (PEG, Molecular weight 100-2,000 Dalton.

1.14 Any of methods 1.10-1.13, wherein the T3 nanoparticles have an average diameter of about 50-1000 nm, e.g., 50-500.

1.15 Any of methods 1.10-1.14, wherein the T3 nanoparticles have an average diameter of about 100-300 nm, e.g., 200 nm.

1.16 Any of methods 1.10-1.15, wherein the T3 nanoparticles have a zeta potential of 0 to −20 mV.

1.17 Any of methods 1.10-1.16, wherein the T3 nanoparticles have a zeta potential of 0 to +20 mV.

1.18 Any of methods 1.10-1.17, wherein T3 is covalently linked to the bioabsorbable polymer.

1.19 Any of methods 1.10-1.18, wherein the nanoparticle comprises a second pharmacologically active ingredient.

1.20 Any of methods 1.10-1.19, wherein the PLGA has a molecular weight range of about 5,000-50,000 Dalton, preferably 6,000-8,000 Dalton.

1.21 Any of methods 1.10-1.20, wherein the PLGA-conjugated to PEG molecular weight range of 5,000-20,000 Dalton, preferably 6,000-8,000 Dalton.

1.22 Any of methods 1.10-1.21, wherein the PLGA-conjugated to PEG molecular weight range of about 6,000-8,000 Dalton.

1.23 Any of methods 1.10-1.22, wherein the T3 is chemically conjugated to PLGA or PLGA-PEG for assembly of Nanoparticles.

1.24 Any of methods 1.10-1.23, wherein the composition is dispersed in a physiological sterile medium.

1.25 Any of methods 1.10-1.24, wherein the composition is dispersed in saline or dextrose.

1.26 Any of methods 1.10-1.25, wherein the biodegradable polymer comprises chitosan.

1.27 Any of the preceding methods, wherein the T3 and PCR are administered via injection.

1.28 Any of the preceding methods, wherein the T3 and PCR are administered via bolus injection.

1.29 Any of the preceding methods, wherein the T3 and PCR are administered via infusion.

1.30 Any of the preceding methods, wherein the T3 and PCR are administered via bolus injection followed by infusion.

1.31 Any of the preceding methods, wherein the T3 and PCR are administered orally.

1.32 Any of the preceding methods wherein the subject is a human.

1.33 Any of the preceding methods, wherein the T3 and PCR is administered together with cardiopulmonary resuscitation (CPR) and/or defibrillation.

In a further aspect, the present disclosure provides for a method [Method 2] for preventing, redirecting or interrupting apoptosis, the method comprising administration of a therapeutically effective amount of triiodothyronine (T3) and phosphocreatine (PCR) to a subject in need thereof. Further embodiments of Method 2 are provided in combination with any of Compositions 1, et seq.

As used herein, T3 refers to triiodothyronine in its naturally occurring form, pictured below:

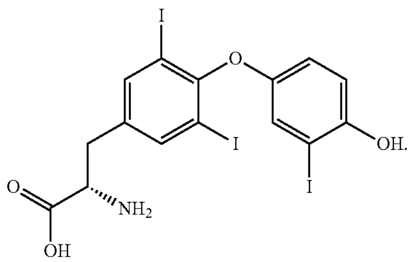 [SMILES: N[C@@H](Cc1cc(I)c(Oc2ccc(O)c(I)c2)c(I)c1)C(=O)O]

T3 is also used herein to refer to triiodothyronine that has been modified at the hydroxyl group stemming from the 4-position on the phenyl ring. For example, T3 as used herein refers to triiodothyronine with a linking group (e.g., a $C_{1-10}$ amine linking group at the hydroxy on the phenyl moiety).

The methods using the composition comprising an effective amount of nanoparticles of T3 and phosphocreatine (PCR), e.g., having the characteristics of any of the foregoing Composition 1 or 1.1-1.16, may be used to treat acute cardiac insufficiency. Examples of cardiac conditions that may be treated include cardiac arrest, cardiogenic shock, and acute heart failure.

For example, while not bound by theory, it is believed that simultaneous delivery of T3-nanoparticles and PCR may act rapidly to restore return of spontaneous circulation while also maintaining ordinary levels of ATP within cardiac myocytes.

In one embodiment, the particles provide a sustained release which allows the T3 to affect gene expression. In another embodiment, the T3 is covalently linked to the bioabsorbable polymer, which reduces the genomic effect and enhances the effect on the integrin receptor.

The T3 nanoparticles of the invention, e.g., having the characteristics of any of the foregoing Composition 1 or 1.1-1.16, may be administered in conjunction with, or adjunctive to, the normal standard of care for cardiac arrest, e.g., cardiopulmonary resuscitation, defibrillation, and epinephrine or for diseases or disorders related to hypoxia, e.g. myocardial hypoxia, stroke (e.g., ischemic stroke or hemorrhagic stroke), traumatic brain injury (e.g., concussion), ischemia (e.g. myocardial ischemia or retinal ischemia), hemorrhagic shock, or edema (e.g., cerebral edema). They may be administered shortly after the cardiac arrest, and optionally later, e.g., 1-24 hours or later, to preserve cardiac and neuronal function.

Various methods of synthesizing T3-nanoparticles are provided. For example, a single emulsion process may produce chitosan-PLGA nanoparticles encapsulating T3. In yet another example, a process involving gelation/conjugation of preformed biodegradable polymers produces 1) chitosan nanoparticles encapsulating T3 with and without glutaraldehyde as a cross-linker; or 2) chitosan-PLGA nanoparticles encapsulating T3. Other cross-linkers may be used.

In yet another example, a process involving chemical bonding of T3 on the surface of PLGA or PLGA-PEG nanoparticles produces 1) PLGA nanoparticles immobilizing T3 or 2) PLGA-PEG nanoparticles immobilizing T3 and additionally including an active compound into the Nano shell such as Phosphocreatine (PCr).

Methods of Making the Compositions of the Present Disclosure

In one embodiment, the T3 is covalently linked to the biodegradable polymer, for example via the hydroxy on the phenyl moiety. Such compositions can be formed using activated T3 which is activated at the phenolic hydroxy with a suitable linker and protected at the amino moiety. For example, in one embodiment, amino-protected T3 is formed using the synthesis as shown in Scheme 1 below.

Scheme 1

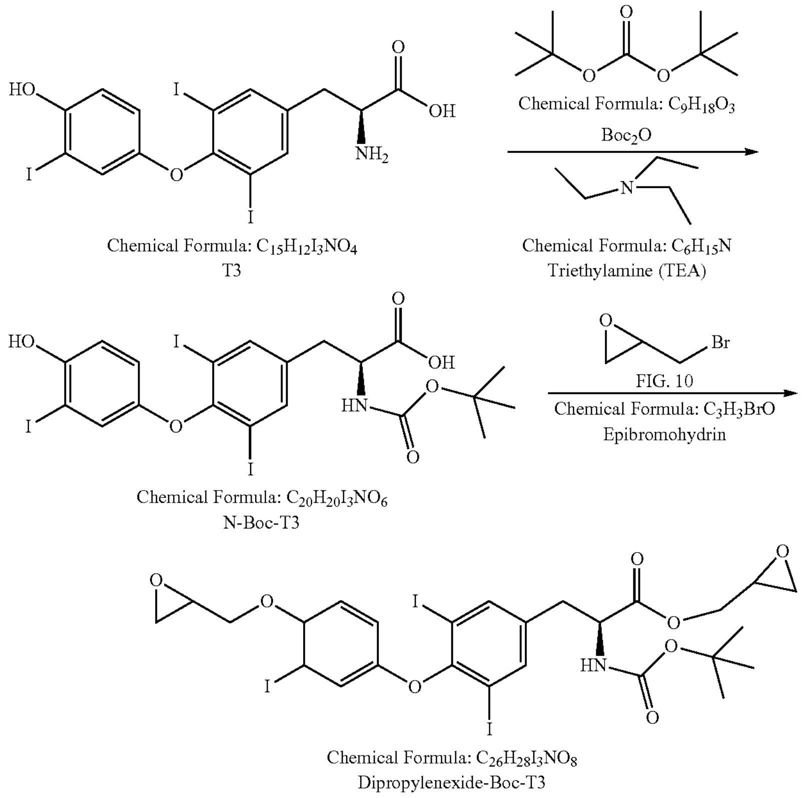

The amino-protected T3 is then linked to the nanoparticle, for example via the phenolic hydroxy, e.g. by using an activated linker group, for example a moiety capable of coupling to an amine group on the bioabsorbable polymer, for example the amino moieties on chitosan.

In one embodiment, therefore, the invention provides activated T3 which is substituted on the phenolic hydroxy group with an epoxide moiety of formula [CH2-O—CH]—[CH2]$_n$- and which is amino protected. For example, the invention provides a compound of formula 1:

Formula 1

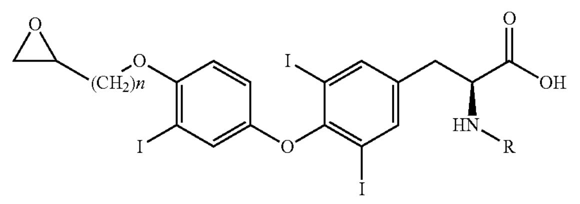

wherein n is an integer selected from 1 through 5, and R is an amino protecting group, e.g., butoxycarbonyl (BOC).

Figure 10:
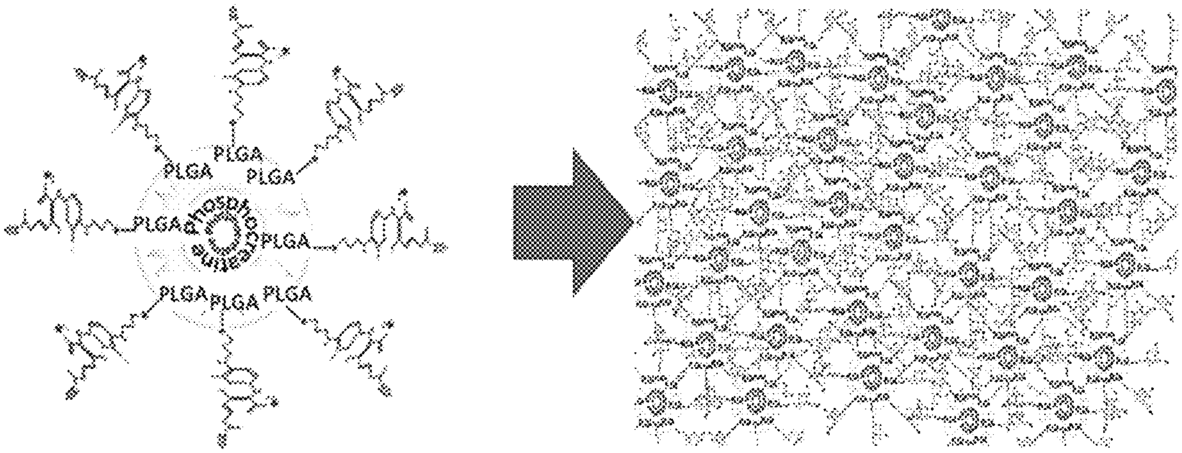
FIG. 10 depicts an embodiment of the form of PLGA nanoparticles of the present disclosure, with T3 bound to the outer surface of the PLGA nanoparticles, and the PCR encapsulated within the nanoparticles.

The T3 may thus be activated, for example using an epoxyalkyl of formula [CH2-O—CH]—[CH2]$_n$-X wherein n=1-5 and X is halogen, e.g. bromine, e.g. according to a synthesis as shown in FIG. 10. The resulting compound is then, if necessary, selectively deprotected to release the carboxy moiety, for example,

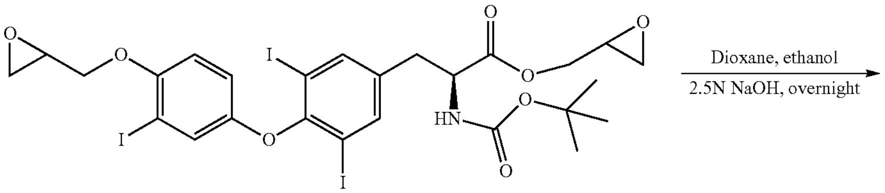

Chemical Formula: $C_{26}H_{28}I_3NO_8$
Dipropyleneoxide-Boc-T3

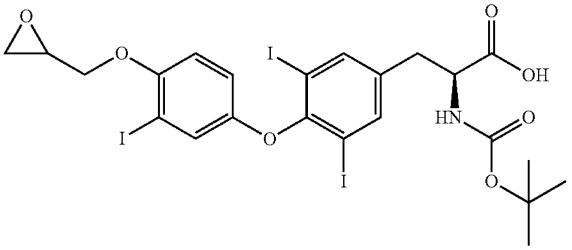

to provide T3 which is activated at the phenolic hydroxy (here, with propylene oxide) and amino-protected (here, with BOC).

Figure 11:
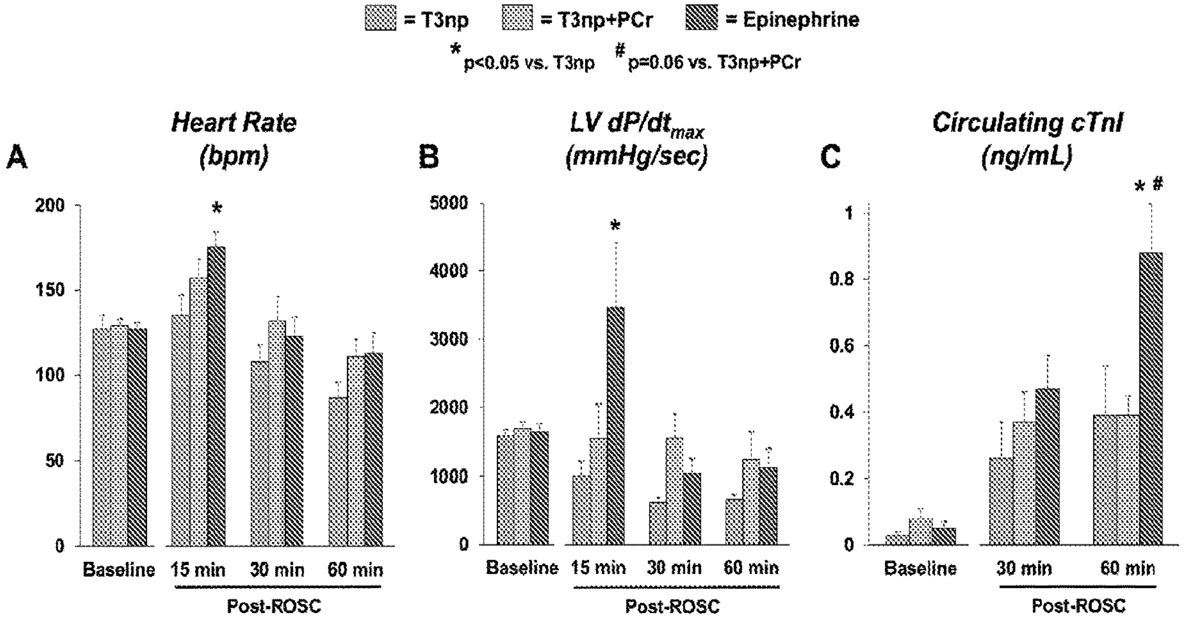
FIG. 11A depicts the observed heart rate in BPM of porcine subjects at periodic intervals following cardiac arrest. Results are shown for porcine subjects treated with T3-nanoparticles, T3-nanoparticles containing phosphocreatine and epinephrine in comparison with the control.
FIG. 11B depicts the observed left ventricle $dP/dt_{max}$ in porcine subjects at periodic intervals following cardiac arrest. Results are shown for porcine subjects treated with T3-nanoparticles, T3-nanoparticles containing phosphocreatine and epinephrine in comparison with the control.
FIG. 11C depicts the observed circulating cTnl in porcine subjects at periodic intervals following cardiac arrest. Results are shown for porcine subjects treated with T3-nanoparticles, T3-nanoparticles containing phosphocreatine and epinephrine in comparison with the control.

The activated T3 is then attached to the bioabsorbable polymer, for example, T3 having an epoxy linker moiety and an amino-protecting group is reacted with a bioabsorbable polymer having amino groups, then deprotected to provide a nanoparticle covalently linked to T3, e.g., as shown in FIG. 11. This reaction may be carried out in the presence of a stabilizer, such as polyvinyl alcohol, e.g. PVA 1% w/v, in an appropriate solvent, for example dimethylsulfoxide, e.g. DMSO (0.1% v/v) and acetic acid (0.1% v/v), which solvents are removed afterwards by dialysis. The number of T3 moieties attached to the nanoparticle may vary based on the reaction conditions and amount of reactant used, but if these conditions are kept constant, the distribution of variation will be low. Typically, the nanoparticle will comprise 20-200 T3 moieties, e.g., about 50 per nanoparticle. The amount of T3 in a batch can be assayed, e.g., as described below, by separating the nanoparticles by filtration or centrifugation, weighing, degrading the T3 nanoparticle in strong base, and measuring by HPLC.

In another embodiment, T3 is covalently linked to the bioabsorbable polymer via a $C_{1-10}$ amine linking group at the hydroxy on the phenyl moiety. The process proceeds generally according to Scheme 2:

Scheme 2

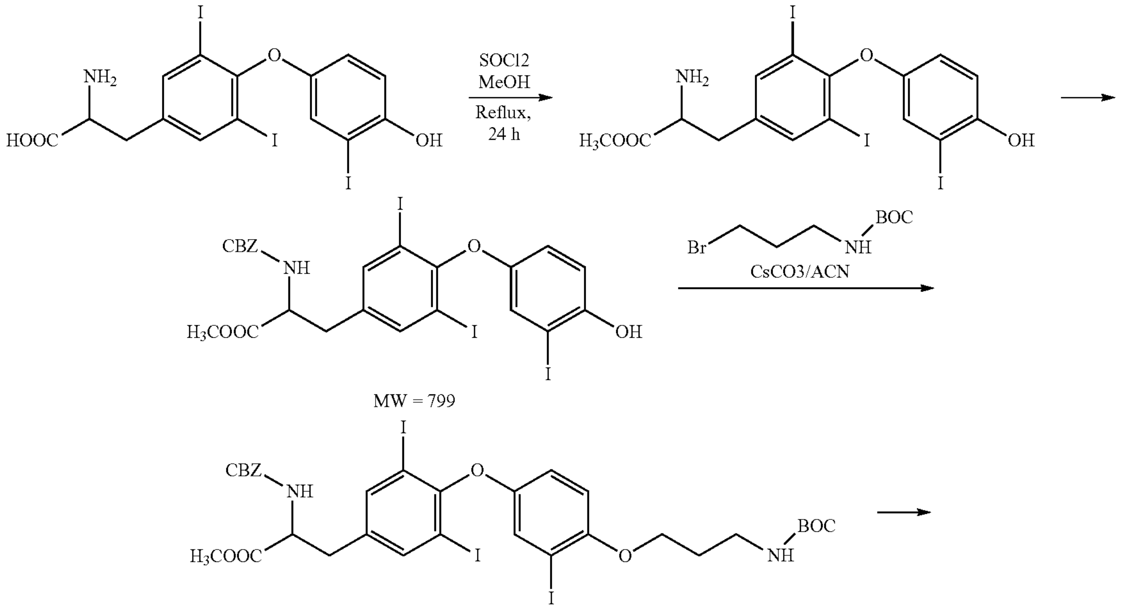

-continued

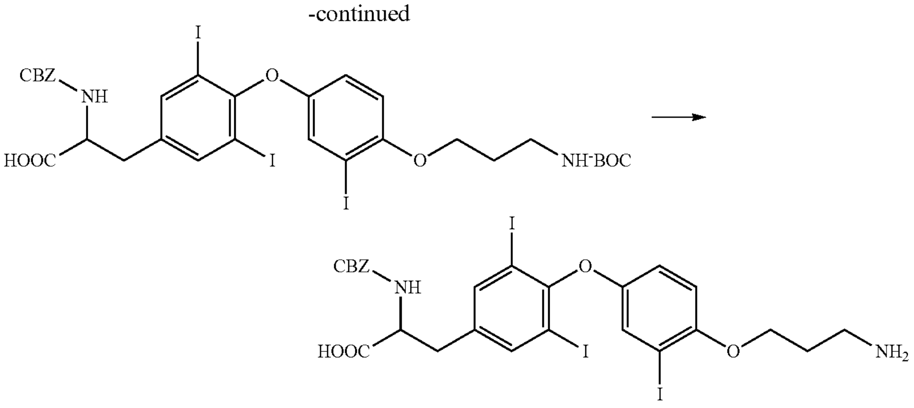

In a first step, T3 is dissolved in anhydrous methanol. Thionyl chloride is then added and the reaction is set to reflux for 24 hours. The reaction is cooled to room temperature and methyl protected T3 is obtained in the form of white powder precipitated and washed by methanol and ether.

In a second step, the methyl protected T3 dissolved in anhydrous methanol. An equivalent of triethylamine (TEA) is added to the solution and stirred for a half hour. An equivalent of benzyl chloroformate (CBZ) is then added and stirred for 6 hours at room temperature. The methanol is removed and the product is extracted by dichloromethane (DCM) and washed by acidic water, bicarbonate and brine.

In a third step, a mixture of the CBZ-protected T3, 3-bromopropylamine protected with tert-butyloxycarbonyl (BOC) and potassium carbonate (5 eq) in acetone was heated at reflux for 24 hours. The reaction was filtered, concentrated, and then crude purified with flash column chromatography over silica gel using n-hexane and ethyl acetate (9:1 to 7:3) to give final product.

The BOC protecting group is removed, followed by removal of the methyl protecting group, until the T3 is protected only with the CBZ group. The T3 is mixed with PLGA functionalized with N-hydroxysuccinimide (NHS) in TEA and dimethylsulfoxide (DMSO). The resulting product is T3 covalently bound to PLGA, and the CBZ protecting group is removed.

Nanoparticle production is generally described in the Applicant's own publications: US 20110142947 A1, and WO 2011/159899, as well as application number U.S. Ser. No. 13/704,526, the contents of each of which are incorporated herein by reference in their entireties. Nanoparticles as described herein may be produced by similar means.

Without being bound by theory, it is believed that the T3 and phosphocreatine containing nanoparticles take the form illustrated in FIG. 10. In brief, T3 molecules having a suitable linking group (e.g., a $C_{1-10}$ amine linking group) are covalently bound to the outer surface of PLGA nanoparticles. In addition, phosphocreatine is encapsulated within the PLGA nanoparticle.

In one example, the T3 nanoparticles are made from T3 and the following components:

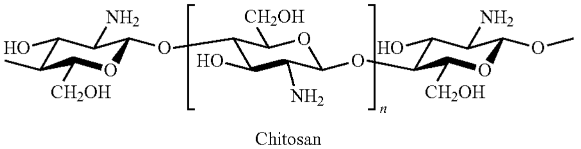

Chitosan

-continued

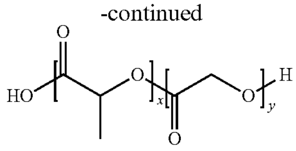

PLGA

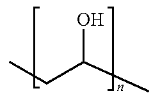

PVA (stabilizer)

In one example, the nanoparticles have these components in approximately the following amounts:

| Components of the formulation | Amount (% w/w) | Role in the formulation |
|---|---|---|
| PLGA or PLGA-PEG | 80-99%, e.g. 90% | Component of the nanocarrier |
| T3 | 1-20%, e.g. 5% | Active ingredient (chemically conjugated to the nanoparticles) |

The contents of the nanoparticles are confirmed using, e.g. DLS, TEM, NMR, HPLC and LC/MS. The nanoparticle formulations may be sterilized using conventional means, e.g., filtration, gamma radiation.

The above measurements (i.e., viscosity) may be carried out by any means known in the art. For example, it is contemplated that the viscosity of chitosan solutions may be measured at room temperature using a Brookfield type digital viscometer, e.g., DV-11+Pro. In another example, it is contemplated that the viscosity may be measured using a Ubbelohde type viscometer. In such an example, it is contemplated that the viscometer could be connected to a visco-clock to record the time of the passing solution.

EXAMPLES

Example 1: Cardiovascular Protective Effect of Nanoparticles of T3 and Phosphocreatine Against Ischemic Insults This study aimed to investigate the positive protective role of T3, T3 nanoparticles and nanoparticles of T3 and phosphocreatine (PCR) in hypoxia-mediated cardiac cell insults, as well as its influences on vascularization and neuronal protection, under hypoxic condition. The effects of T3 and T3 nanoparticles+PCR on angiogenesis were studied in a CAM model. The cardioprotective effect of T3 under hypoxia was studied using isolated neonatal cardiomyocytes which were treated with PBS (control), free T3 (3 uM), free PCR (30 uM) and T3 nanoparticles+PCR. Mitochondrial function and sarcomere integrity were studied using an ATP-bioluminescence assay, and cardiac Troponin T levels using flow cytometry, respectively. The effect of T3 nanoparticles on induced neuronal cells under hypoxia was also studied. Finally, T3 and T3 nanoparticles tagged with Cy7 dye were injected into mice tail veins to monitor their biodistribution in real time.

The results of the test are shown in FIG. 1. T3 and T3 nanoparticles enhanced angiogenesis in a CAM model (~3 fold) compared to the control group. Under hypoxia, cardiac ATP improvement was achieved only with the combination of T3 nanoparticles and PCR ($p<0.001$) while maintaining normal Troponin T levels. The T3 nanoparticles produced a significant upregulation of the neural protection markers, PAX6 and DLX2 by about 60% and 40%, respectively. In vivo, the Cyamine7 signal intensity was detected primarily in mice brains, and hearts, within minutes of administration, showing that the composition containing T3 nanoparticles with PCR was also unexpectedly able to cross the blood brain barrier.

The T3 nanoparticles works on the activation of the cell surface receptor $\alpha v\beta 3$ and is distributed into the cytoplasm, but not the nucleus. Compositions of T3 nanoparticles+PCR therefore represents a potentially new therapeutic for the control of tissue damage in cardiac ischemia and resuscitation.

Example 2: Synthesis and Size Comparison for Different Nanoparticle Bases

Several different potential polymer bases were created for the nanoparticles. PLGA base nanoparticles containing T3 were created by dissolving 200 mg PLGA and 20 mg T3 in 1 mL DMSO. The solution was added dropwise to 40 mL of 1% PVA under sonication. The emulsion was freeze dried and DMSO was removed. The product was then reconstituted in 20 mL PBS.

A similar method was carried out to create PLGA base nanoparticles containing T3 and PCR. PLGA base nanoparticles containing T3 were created by dissolving 250 mg PLGA and 25 mg T3 in 1 mL DMSO. The solution was added dropwise to a solution of 20 mL 1% PVA containing 45 mg PCR under sonication. The resulting emulsion is then added to 30 mL 1% PVA dropwise. The emulsion was freeze dried and reconstituted in 25 mL PBS.

PLGA-PEG base nanoparticles were also created. A mixture of PLGA-PEG and T3 was added dropwise to a 1% solution of PVA. The contents are sonicated and lyophilized to yield PLGA-PEG-T3 nanoparticles. PCR is optionally added to the resulting emulsion prior to lyophilization in a 1% solution of PVA to create PLGA-PEG-T3 nanoparticles that encapsulate PCR.

Each base was measured via dynamic light scattering for particle size. The results are summarized below in Table 1.

TABLE 1

Particle size for NP bases

| Sample | Avg. diameter (nm) | PDI |
|---|---|---|
| Void-PLGA nanoparticles | 179 | 0.141 |
| PLGA-PEG-Phosphocreatine nanoparticles | 157 | 0.132 |
| L-T3-Phosphocreatine-PLGA nanoparticles | 181 | 0.136 |
| L-T3-PLGA nanoparticles | 185 | 0.115 |

As shown in the table above, all forms of nanoparticles show similar average diameters. The PLGA nanoparticles without T3 or PCR showed a diameter of 179 nm, which was similar to the L-T3-Phosphocreatine-PLGA (181 nm) and L-T3-PLGA nanoparticles (185 nm). The PLGA-PEG base showed a somewhat smaller, but comparable diameter at 157 nm. FIGS. 2-5 illustrate the particle size distribution for each of the bases created.

Release kinetics were also studied for PLGA and PLGA-PEG base nanoparticles. It was observed that the PLGA nanoparticle had a superior rate of release for active agents in comparison with the PLGA-PEG base nanoparticle.

Example 3: Cardiovascular Protective Effect of Nanoparticles of the Present Disclosure Against Ischemic Insults Studies were carried out to investigate the positive protective role of nanoparticles comprising both T3 with PCR in hypoxia-mediated cardiac cell insults, as well as its influences on vascularization and neuronal protection, under hypoxic conditions.

The effects of T3 and Nano-T3+Pcr on angiogenesis were studied in a chick embryo chorioallantoic membrane (CAM) model. It was observed that T3 and Nano-T3 enhanced angiogenesis in a CAM model (~3 fold) compared to the control group. Results are summarized below in Table 2.

TABLE 2

Observed Angiogenesis for samples treated with T3 or Nano-T3

| Sample | Branch points (SEM) |
|---|---|
| PBS (vehicle) | 45.3 ± 5.2 |
| bFGF | 115.4 ± 3.2 |
| T3 (10 μg) | 158.4 ± 5.5 |
| Nano-T3 (1 μg) | 185.5 ± 4.2 |

Both T3 and T3 nanoparticles showed greatly enhanced angiogenesis in comparison with samples treated with basic fibroblast growth factor. In comparison to the bFGF, T3 alone showed a 37% improvement in observed branch points and T3 bound to PLGA nanoparticles showed a 61% improvement in comparison with bFGF treated samples.

The cardioprotective effect of T3 under hypoxia was then studied using isolated neonatal cardiomyocytes which were treated with PBS (control), T3 (1-3 uM), T3 and PCR (5 μM), T3 nanoparticles (1-3 μM), T3 and PCR nanoparticles (5 μM), and epinephrine (0.5 μM). The cells were cultured in a hypoxia incubator with 4% oxygen, 5% $CO_2$ at 37° C. for 24 hours. Following incubation, the cells were collected and compared with those of normal condition. Mitochondrial function and sarcomere integrity were studied using an ATP-bioluminescence assay, and cardiac Troponin T levels using flow cytometry after adding troponin T antibody conjugated with FITC.

Under hypoxia, cardiac ATP improvement was achieved with NT3+Pcr ($p<0.001$) while maintaining normal Troponin T levels. As shown in Table 3 below, epinephrine showed contraction levels in cardiomyocytes similar to cells in the hypoxic state, while T3 and Nano-T3 treated samples showed contraction levels close to those of the cells under normal conditions.

TABLE 3

Effect of Nano-T3 and Phosphocreatine on neonatal cardiomyocyte contraction under normoxic and hypoxic condition

| Cardiomyocyte Treatment | Contraction/min | Rhythm |
|---|---|---|
| Untreated (normoxia) | 160 | Regular |
| Nano-T3 (normoxia) | 186 | Regular |
| Nano-T3 + PCR (normoxia) | 180 | Regular |
| Epinephrine (normoxia) | 186 | Regular |
| Untreated (hypoxia) | 39 | Irregular |
| Nano-T3 (hypoxia) | 134 | Regular |
| Nano-T3 + PCR (hypoxia) | 145 | Regular |
| Epinephrine (hypoxia) | 28 | Irregular |

Figure 6:
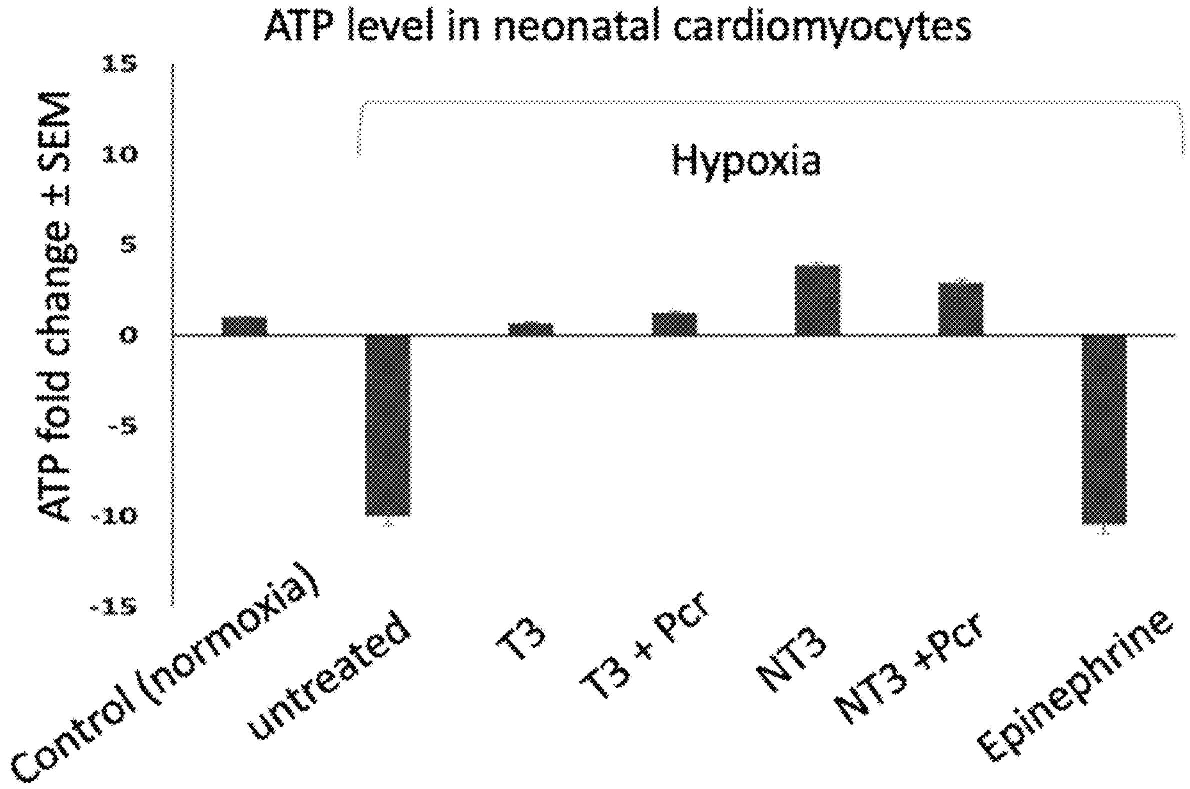
FIG. 6 depicts the cardioprotecive effect of Nano T3 in normal vs hypoxic condition in terms of ATP levels in neonatal cardiomyocytes (bioluminescence assay).
Figure 7:
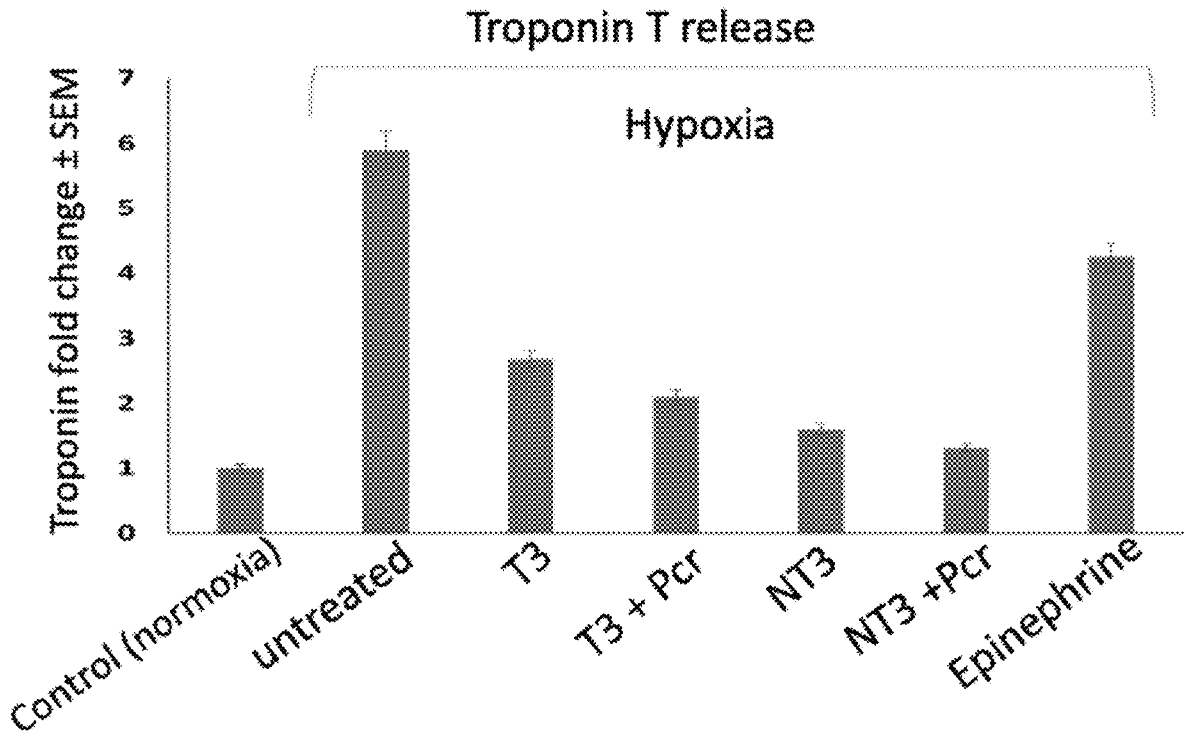
FIG. 7 depicts the cardioprotecive effect of Nano T3 in normal vs hypoxic condition in terms of Troponin T release levels in neonatal cardiomyocytes (bioluminescence assay).

These results are generally consisted with observed levels of ATP and troponin following treatment with T3 and PCR in nanoparticle form. FIG. 6 illustrates the effect that treatment of T3 and PCR had on ATP levels in myocytes, and FIG. 7 illustrates the effect that T3 and PCR had on troponin levels. In both cases, treatment with epinephrine showed ATP and troponin release levels close to untreated hypoxic cardiomyocytes, while treatment with both T3 nanoparticles and T3 and PCR nanoparticles showed results close to control cardiomyocytes under ordinary oxygen conditions. T3 and Nano-T3 was associated with approximately close results, but Nano-T3 has a better delivery.

Figure 8:
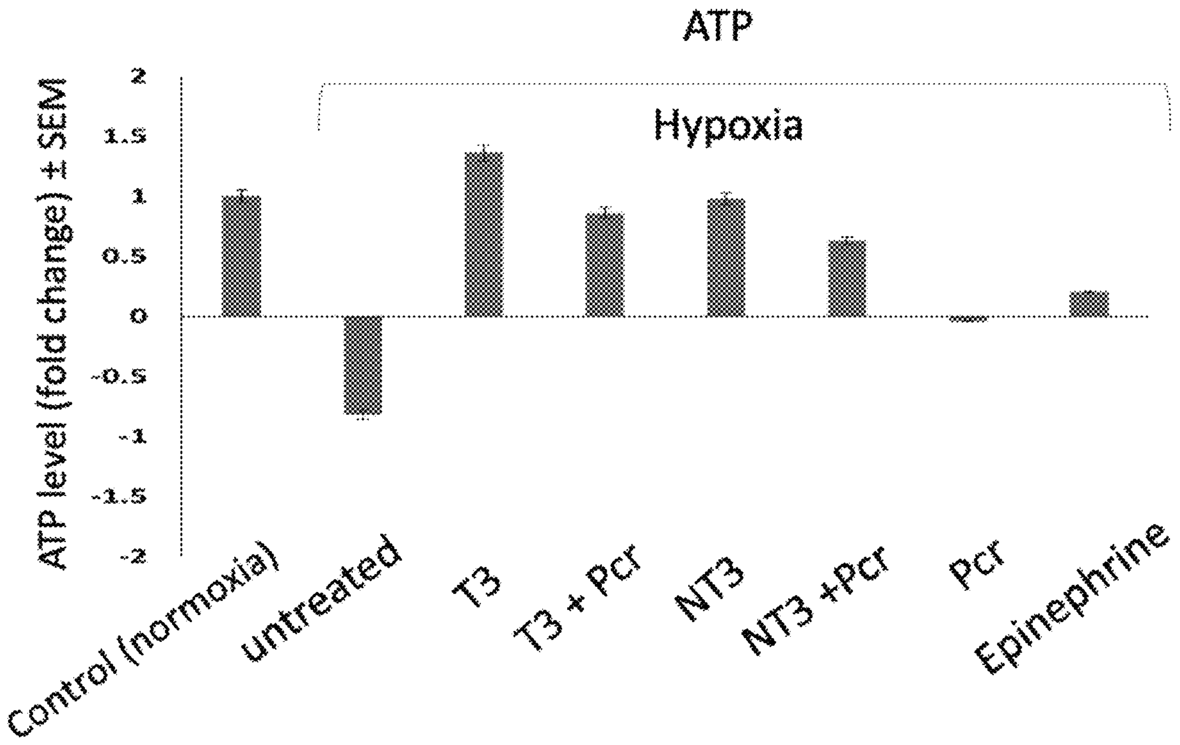
FIG. 8 depicts the effect of T3, Nano T3, and Nano T3 and phosphocreatine on Neuronal (PC12) cells under hypoxia in terms of ATP levels.
Figure 9:
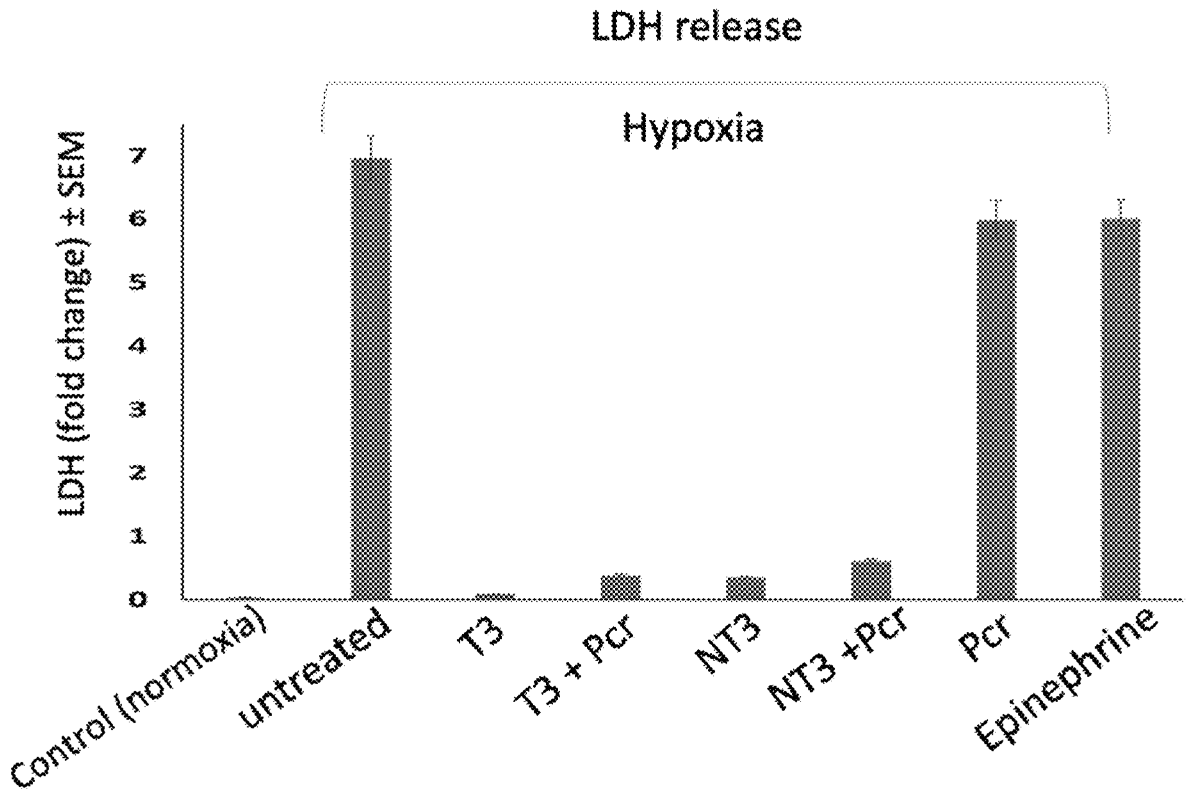
FIG. 9 depicts the effect of T3, Nano T3, and Nano T3 and phosphocreatine on Neuronal (PC12) cells under hypoxia in terms of Troponin T release levels.

The effect of T3 nanoparticles on induced neuronal cells under hypoxia was also studied. Results are summarized in FIGS. 8 and 9. The results show ATP levels and lactate dehydrogenase release in PC12 neuronal cells treated with Nano-T3 and Nano-T3 and PCR levels similar to cells under ordinary oxygen conditions. It was further observed that Nano-T3 produced a significant upregulation of the neural protection markers, PAX6 and DLX2 by about 60% and 40%, respectively.

Example 4: A Blinded, Randomized, Vehicle-Controlled Preclinical Trial of Novel Nanoparticle Formulations of Triiodothyronine in Cardiac Arrest In another study, the inventors evaluated the efficacy of two nanoparticle formulations of T3 designed to prolong cell membrane-mediated signaling in a porcine cardiac arrest model. In this study, swine were subjected to 7 minutes of cardiac arrest followed by manual CPR for up to 20 minutes with defibrillation every 2 minutes as necessary. Two minutes after initiation of CPR, animals were randomized to intravenous vehicle (empty PLGA nanoparticles), Nano-T3 (nanoparticles covalently bound to T3; 0.125 mg/kg), Nano-T3 and PCR (nanoparticles covalently bound to T3 with encapsulated PCR; 0.125 mg/kg) or Epinephrine (0.015 mg/kg) in a blinded fashion (n=10/group). In animals that achieved ROSC (unassisted systolic BP>80 mmHg for 1 min), further pharmacologic support was limited to 1 additional dose of the selected drug for hypotension. Hemodynamics, left ventricular (LV) function, plasma cardiac troponin I (cTnl) and other parameters were assessed at baseline and for up to 4 hours post-ROSC.

Figure 12A:
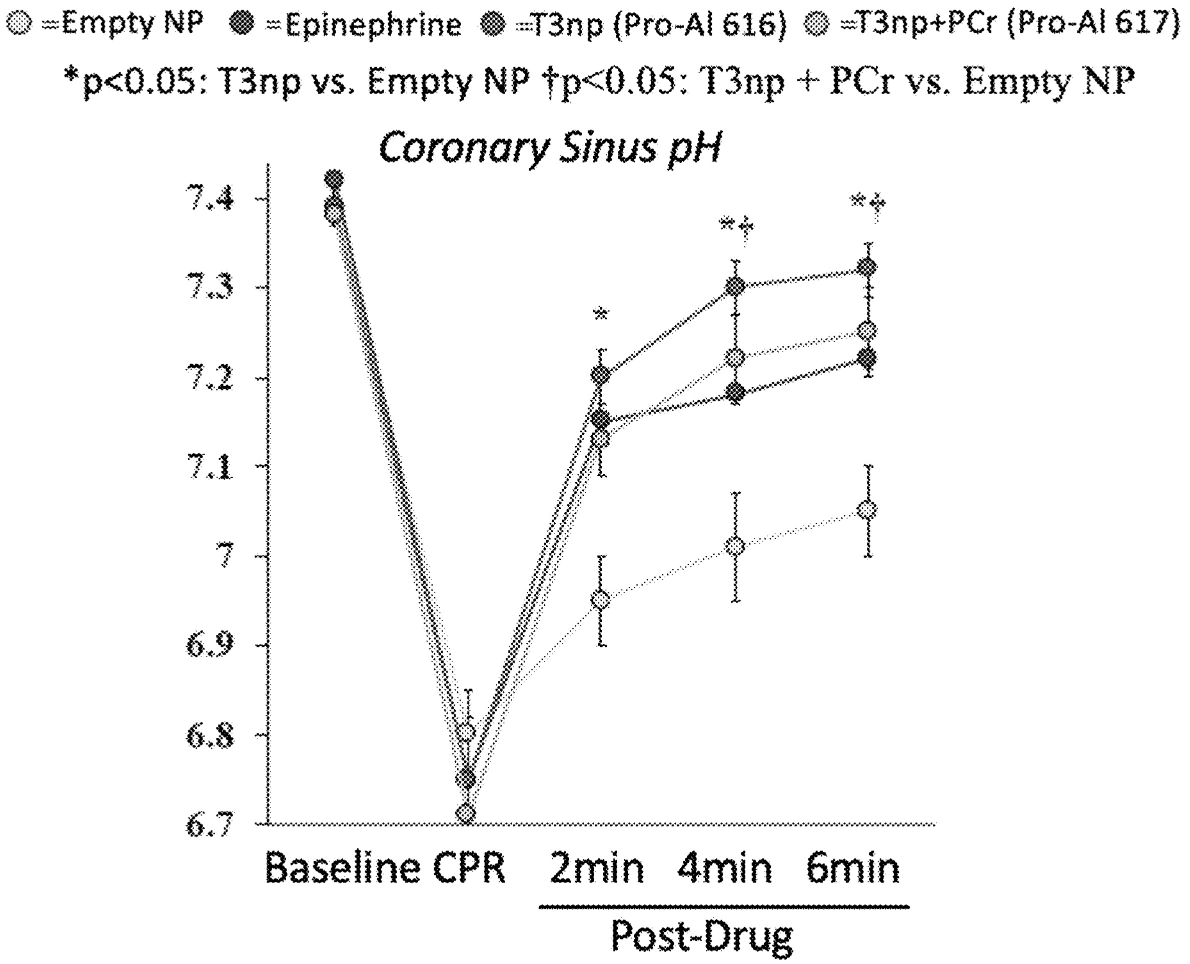
FIG. 12A depicts the observed coronary sinus pH of porcine subjects at periodic intervals following cardiac arrest. Results are shown for porcine subjects treated with T3-nanoparticles, T3-nanoparticles containing phosphocreatine and epinephrine in comparison with the control.
Figure 12B:
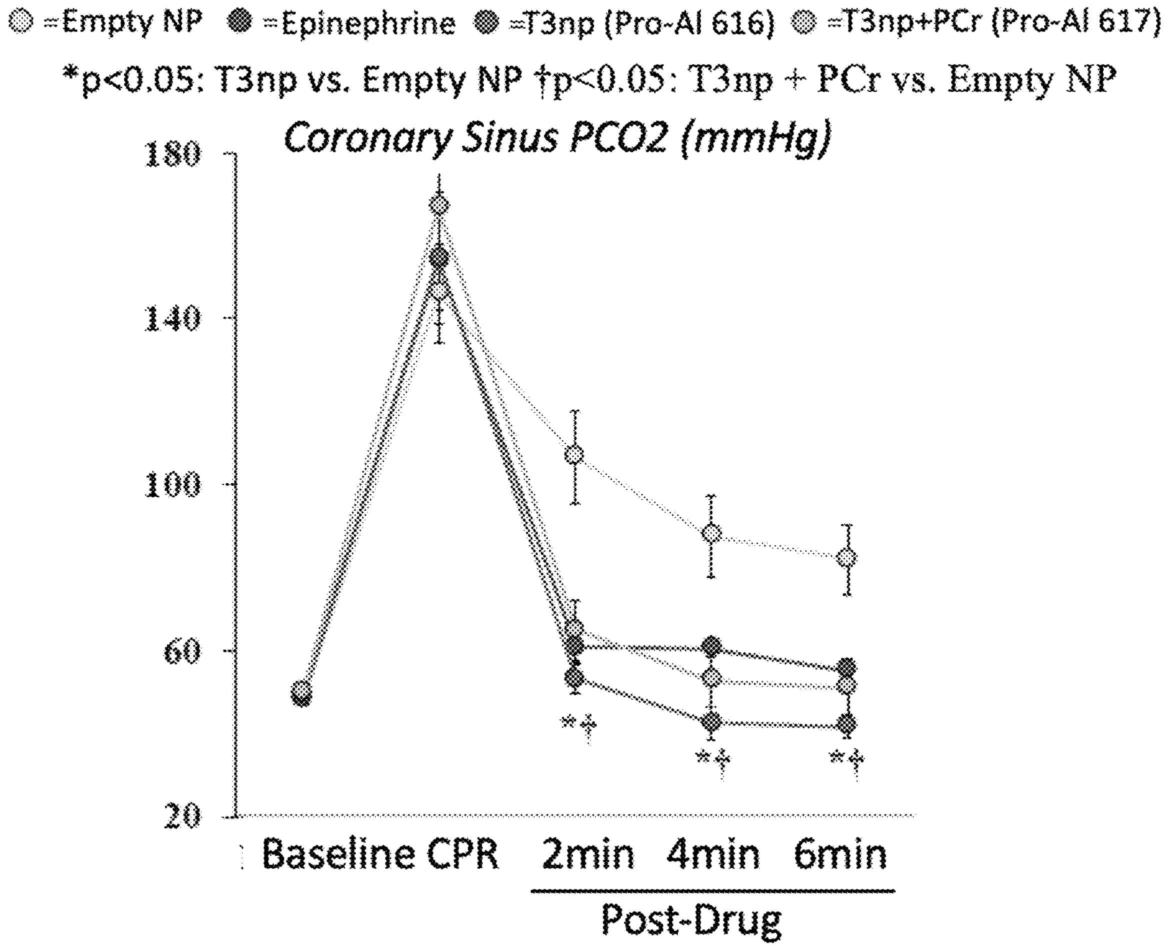
FIG. 12B depicts the observed coronary sinus $pCO_2$ of porcine subjects at periodic intervals following cardiac arrest. Results are shown for porcine subjects treated with T3-nanoparticles, T3-nanoparticles containing phosphocreatine and epinephrine in comparison with the control.

Compared with vehicle, the rate of ROSC was higher in animals receiving Nano-T3, Nano-T3 and PCR or epinephrine. Early after ROSC, Nano-T3 treated animals exhibited a lower heart rate and LV dP/dtmax vs. epinephrine-treated animals, but differences were no longer apparent 30-60 min post-ROSC (see FIGS. 11A and 11B). Analysis of coronary sinus blood samples collected shortly after drug administration demonstrated that Pro-Al 616 and Pro-Al 617, but not epinephrine, produced a significant improvement in coronary sinus pH and PCO2 compared to vehicle within the first 5 minutes post-ROSC (see FIGS. 12 and 13).

Although survival duration was comparable between groups (Nano-T3: 122±30 min, Nano-T3 and PCR: 119±22 min, epinephrine: 116±26 min), epinephrine was associated with a 2-fold higher concentration of cTnl indicative of more severe myocyte injury (C). The results showed that the tested nanoparticles achieved a ROSC rate and post-ROSC survival that was superior to vehicle and comparable to epinephrine. However, the significant reduction in post-ROSC cTnl levels in comparison with epinephrine suggests that resuscitation with Nanoparticles containing T3 and PCR may lead to more favorable clinical outcomes in cardiac arrest. Further electron microscopy analysis showed improvement after treatment with both Nano T3 or Nano T3/PCR in comparison with free T3 alone.

Example 5: Neuroprotective Effect of Nano-T3 and Phosphocreatine in the Brain Quantification of brain injury biomarkers and histopathological evaluation of brain tissue is performed using commercially available assays designed to quantify circulating concentrations of human brain injury biomarkers, including S100 calcium-binding protein B (S100B), phosphorylated neurofilament-H (pNF-H), neuron-specific enolase (NSE), and creatine kinase brain band (CK-BB). Assays are selected for use with samples collected from animals that are studied in the cardiac arrest model of Example 4.

Brain tissue samples are analyzed using light microscopy as well as electron microscopy. Light microscopy of formalin-fixed tissue samples and electron microscopy of glutaraldehyde-preserved tissue samples of frontal cortex, motor cortex, parietal cortex, hippocampus of all animal subjects. Successful neuroprotective effect will be demonstrated by subjects who show improvement of and/or reduced damage to mitochondrial structure.

Example 6: Neuroprotective Effects of Nano-T3 Against Ischemic Insult

Studies were carried to assess the neuroprotective effect on hypoxic cells following administration of T3 nanoparticles (Nano-T3). HS5 cells were treated with T3 (0.5 μM) to induce neurogenesis, and were then then monitored using flow cytometry. The T3-induced cells and PC12 neuronal cells were treated with T3 (1-3 μM), Nano-T3 (1-3 μM), or Epinephrine (0.5 μM). The cells were then cultured under hypoxia for 24 hours. Results using ATP-bioluminescence and LDH release assays.

Figure 13A:
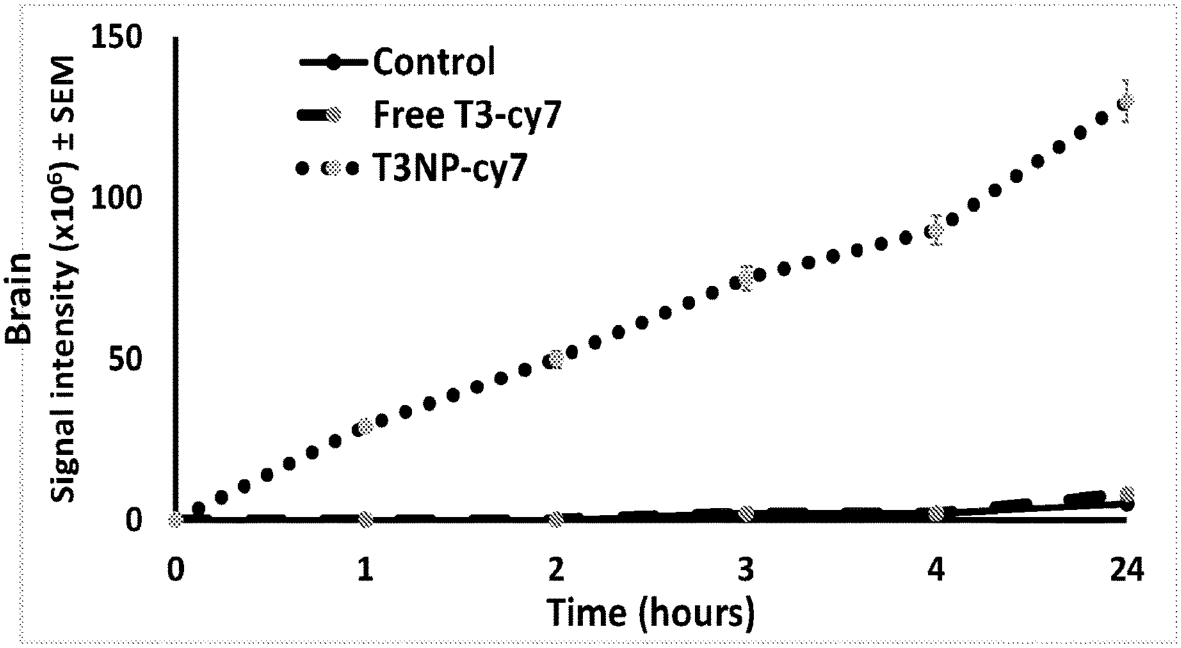
FIG. 13A depicts the bioavailability of Nano-T3 in BALB/C mice brain compared with free T3.
Figure 13B:
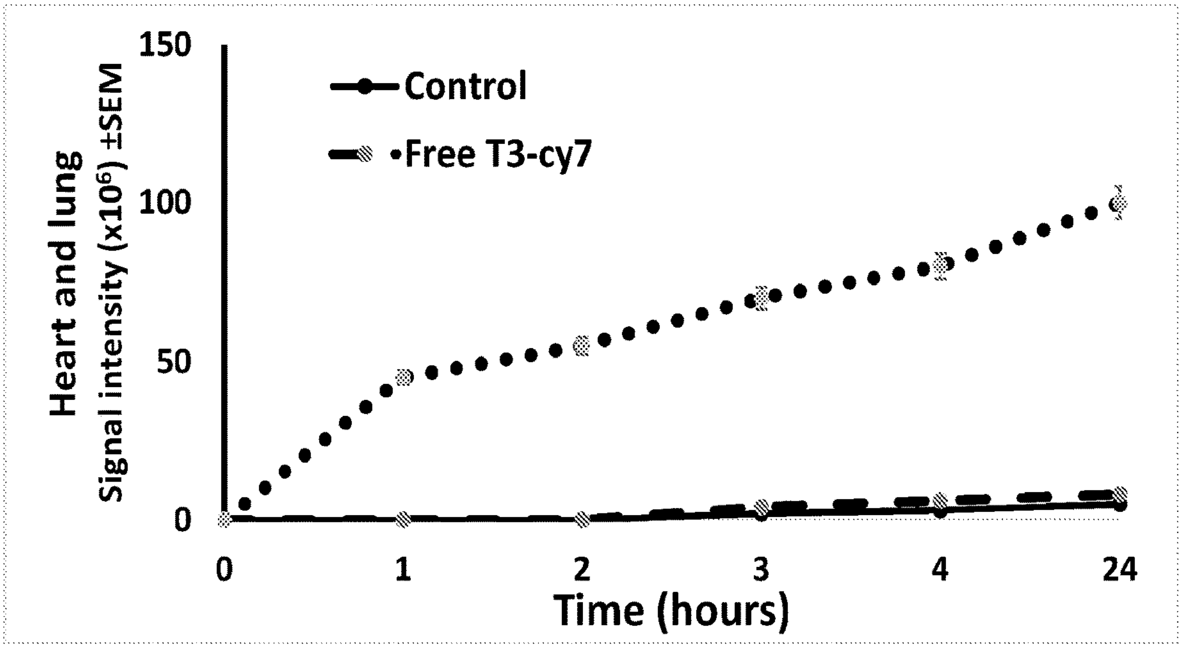
FIG. 13B depicts the bioavailability of Nano-T3 in BALB/C mice heart and lung compared with free T3.

T3 nanoparticles tagged with Cy7 dye were injected into mice tail veins to monitor their biodistribution in real time. Cyamine7 signals were detected with IVIS at excitation/emission maximum 750/776 nm wavelengths. IVIS images were taken to detect Cyamine7 signals directly before injection, immediately at injection, 1 hour post-injection, 2 hours post-injection, 3 hours post-injection, 4 hours post-injection and 24 hours post-injection. As shown in FIGS. 13A and 13B, Nano-T3 was detected at levels significantly higher than T3 and the control, which were barely detected in any of the brain, heart or lungs.

Figure 14:
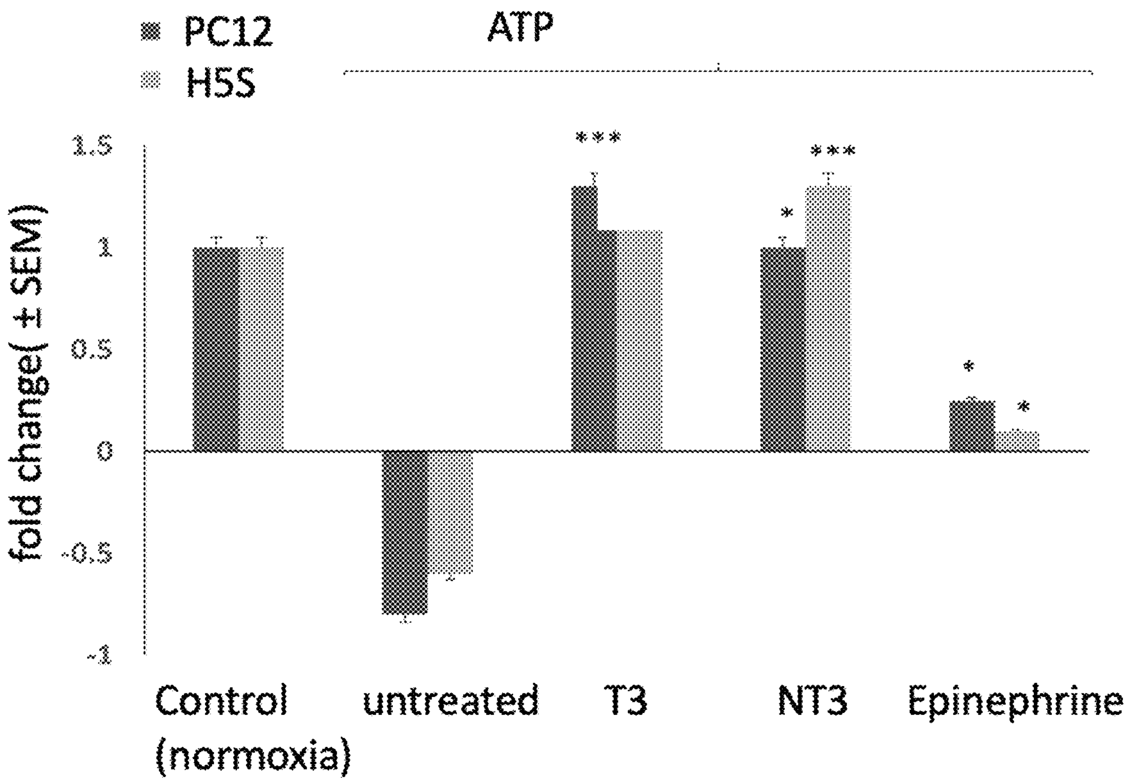
FIG. 14 depicts the effect of T3, Nano T3, and Epinephrine on rat Pheochromocytoma (PC12) cells and T3-induced cells (HS5) under hypoxia in terms of ATP levels.
Figure 15:
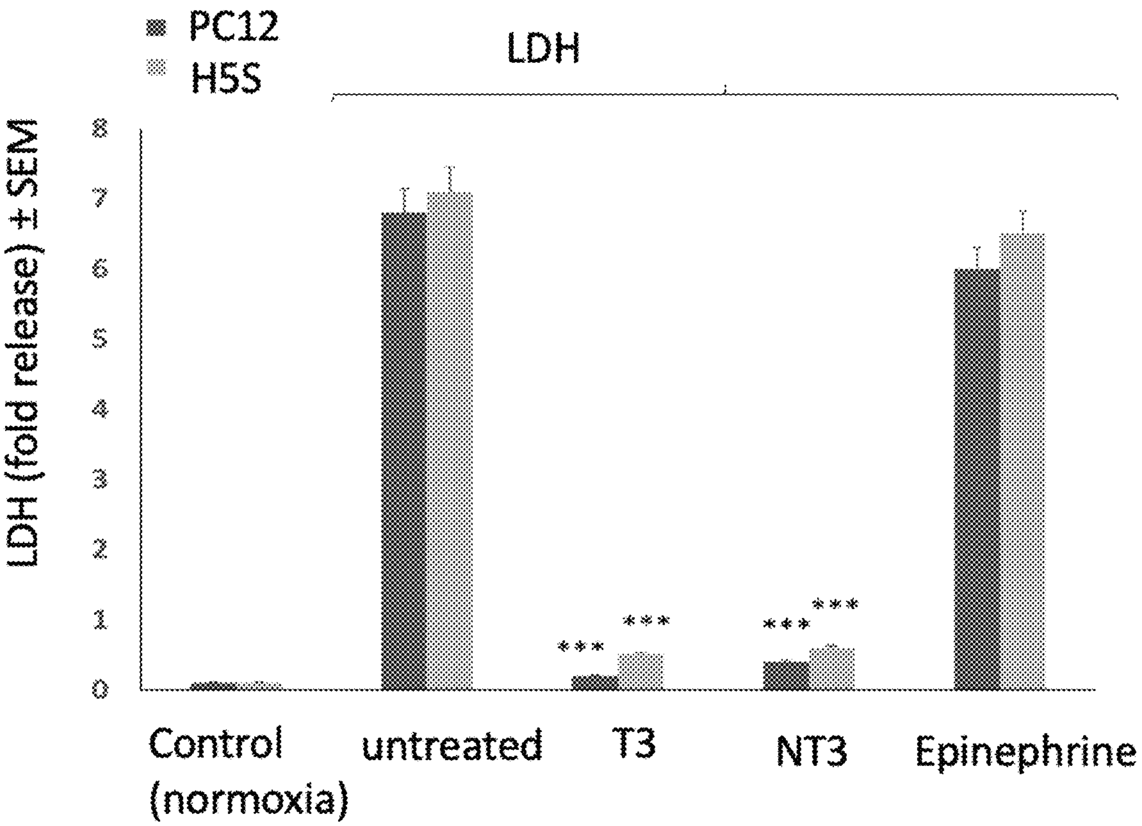
FIG. 15 depicts the effect of T3, Nano T3, and Epinephrine on rat Pheochromocytoma (PC12) cells and T3-induced cells (HS5) under hypoxia in terms of Troponin T release levels.

As illustrated in FIG. 14, under hypoxia (4% oxygen, 5% $CO2$ at 37° C. for 24 hours), ATP levels were increased roughly 1.5-fold in samples treated with Nano-T3 ($P<0.001$), while ATP levels in epinephrine treated samples increased slightly and ATP levels in control decreased. Correspondingly, LDH levels decreased about 6-fold in samples treated with Nano-T3 ($P<0.001$), while epinephrine treated samples showed an increase (FIG. 15). These results are in line with those reported above in Example 3.

Studies were also conducted for detection of neuronal protection markers (PAX6 and DLX2) using flow cytometry. Results showed that forty-eight hours post neuronal induction, PAX6 and DLX2 were upregulated in comparison to control ($P<0.001$). At day 7, PAX6 showed a significant decrease (45% less than control) (**$P\leq 0.001$) while DLX2 showed significant increase (90%) (±$P\leq 0.001$). However, the cell samples treated with Nano-T3 showed approximately a 50% increase in PAX6 and DLX2 expression (60% and 40% expression of PAX6 and DLX2, respectively) after 7 days of neuronal induction, indicating a neuroprotective effect.

Thus, Nano-T3 positively affected neurogenesis and cytoprotection through the induction of different neural transcription factors. These results suggest that Nano-T3 represents a potentially new therapeutic route for the control of tissue damage in brain ischemia, in addition to the cardioprotective and revascularization effects discussed above.

Example 7: Histopathological Analysis of Hypoxic Pig Brain Tissue

Figure 16:
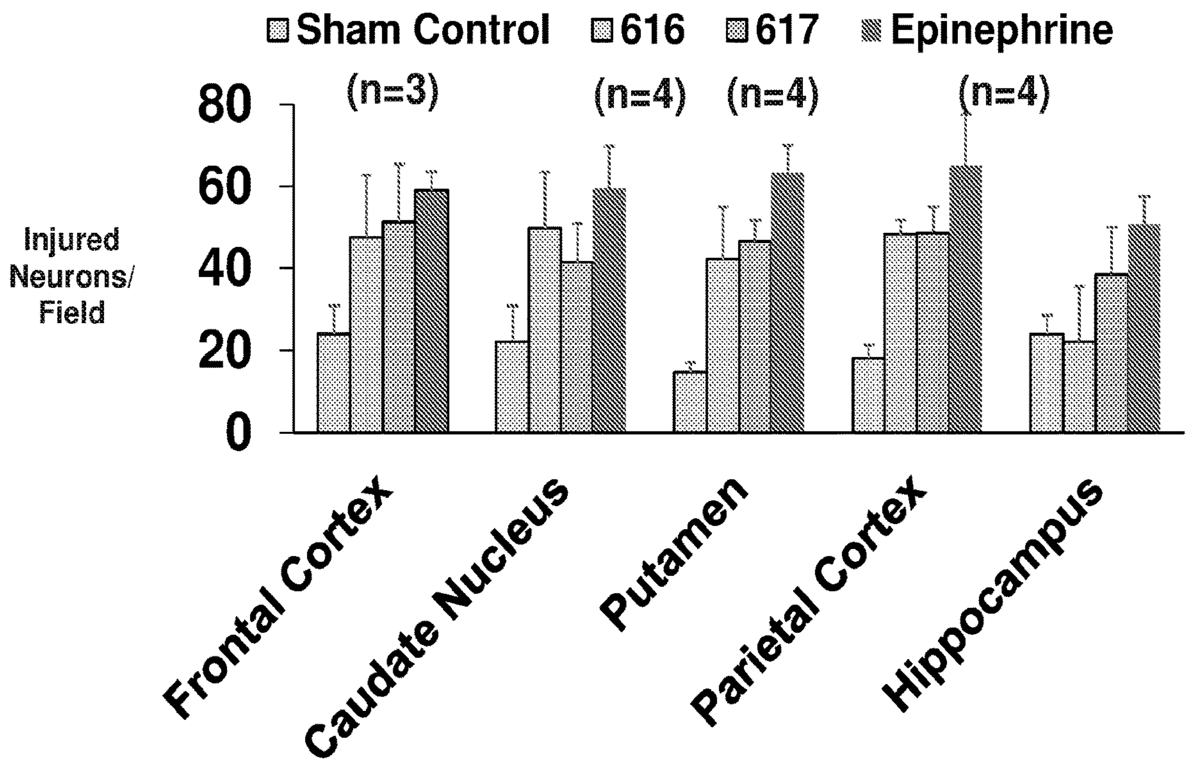
FIG. 16 depicts the neuroprotective effect of Nano-T3 and Nano-T3/PCR on pig brain tissue following cardiac arrest and resuscitation compared with epinephrine.

The effect of Nano-T3 and nanoparticles of T3 and phosphocreatine (Nano-T3/PCR) on brain tissue damage following hypoxic insult was assessed in pigs. The animals were subjected to cardiac arrest for a period of 7 minutes. Following this time, the animals were resuscitated with one of Nano-T3, Nano-T3/PCR or epinephrine. Analysis of brain tissue was carried out on animals that were resuscitated and survived for 4 hours. Normal pigs were used as a control. Brain tissue samples were resected from the frontal cortex, caudate nucleus, putamen, parietal cortex and the hippocampus of each animal. The sections were then set on slides in formalin and paraffin, and were analyzed with an Aperio slide scanner. Neuronal injury was quantified as number of cells damaged due to ischemia. Results are summarized in FIG. 16.

As illustrated, the samples treated with Nano-T3 (i.e., labeled "616" in FIG. 16) and Nano-T3/PCR (i.e., labeled "617" in FIG. 16) showed fewer cells injured by ischemia over the tissue samples treated with epinephrine from each tested region of the brain.

Example 8: Effect of Nano-T3 and Nano-T3/PCR on Release of Neuron-Specific Enolase A further study was carried out to test the effect of Nano-T3 treatment on the expression of Neuron-Specific Enolase (NSE) in pig blood plasma using a SimpleStep Human Neuron specific Enolase ELISA Kit (Abcam ab217778), since the antibody used in the assay cross-reacts with porcine NSE.

The blood samples were collected from pigs subjected to cardiac arrest and resuscitation as described in Example 7. Following 7 minutes of cardiac arrest, the animals were resuscitated with Nano-T3, Nano-T3/PCR or epinephrine. At 2 hours post-ROSC, blood samples were collected from a peripheral vein into tubes with EDTA and centrifuged for 15 minutes. The plasma samples were then used for the NSE assay based on the manufacturer's instructions.

Figure 17:
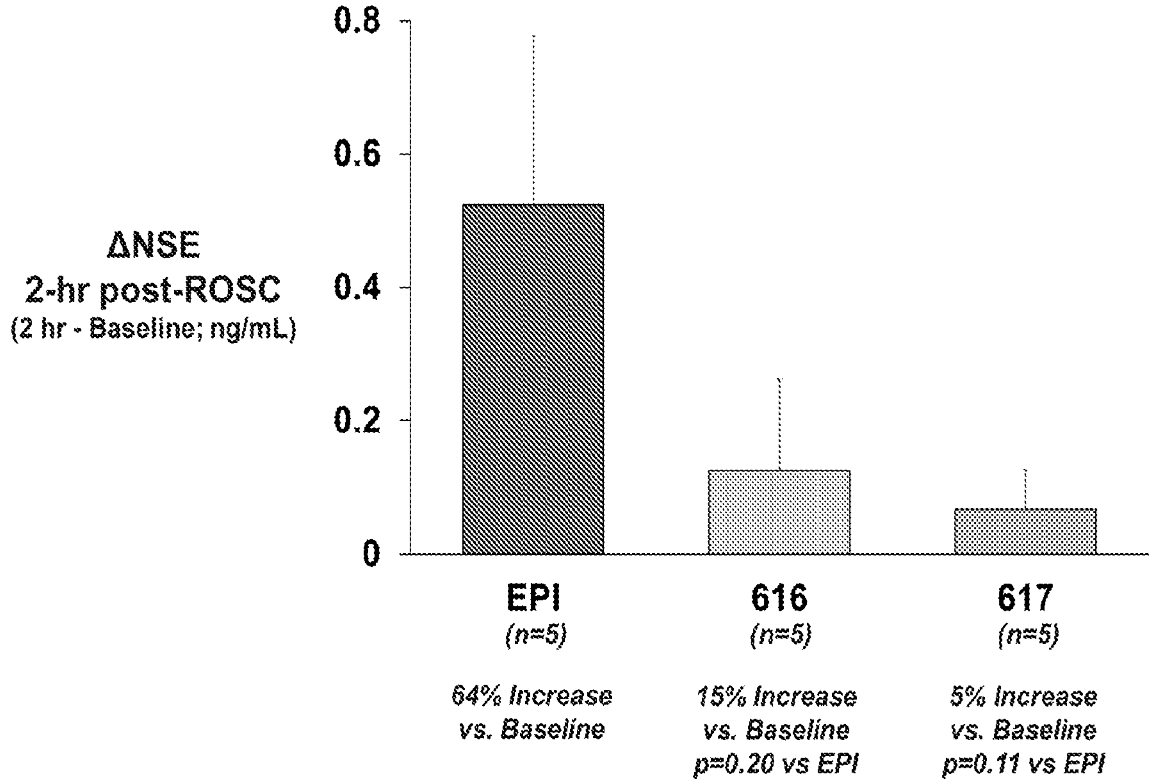
FIG. 17 depicts the effect of Nano-T3, Nano-T3/PCR and epinephrine on the release of neuron-specific enolase.

The results are summarized in FIG. 17. As shown, samples treated with Nano-T3 (i.e., labeled "616" in FIG. 17) and Nano-T3/PCR (i.e., labeled "617" in FIG. 17) showed significant reduction in circulating NSE. Specifically, while epinephrine-treated samples showed a 64% increase of NDE over baseline, while Nano-T3 and Nano-T3/PCR treated samples showed only 15% and 5% increases, respectively.

Alternative combinations and variations of the examples provided will become apparent based on this disclosure. It is not possible to provide specific examples for all of the many possible combinations and variations of the embodiments described, but such combinations and variations may be claims that eventually issue.

The invention claimed is:

1. A composition comprising nanoparticles of T3 and phosphocreatine (PCR) encapsulated or immobilized by a biodegradable polymer.

2. The composition of claim 1, wherein the nanoparticles comprise the T3 conjugated by covalent bonding to the biodegradable polymer and the phosphocreatine (PCR) encapsulated within the biodegradable polymer.

3. The composition according to claim 1, wherein the polymer comprises poly (lactic-co-glycolic acid) (PLGA) or polylactic acid (PLA).

4. The composition according to claim 3, wherein the PLGA has a molecular weight range of 5,000-50,000 Dalton; and wherein the T3 is optionally chemically conjugated to PLGA or PLGA-PEG for assembly of nanoparticles.

5. The composition according to claim 1, wherein the T3 nanoparticles have an average diameter of 50-1000 nm.

6. The composition according to claim 1, wherein the T3 nanoparticles have an average diameter of 100-300 nm.

7. The composition according to claim 1, wherein the T3 nanoparticles have a zeta potential of 0 to −20 mV, or 0 to +20 mV.

8. The composition according to claim 1, wherein T3 is covalently linked to the biodegradable polymer.

9. The composition according to claim 1, wherein the nanoparticles comprise a second pharmacologically active ingredient.

10. The composition according to claim 1, wherein the composition is dispersed in a physiological sterile medium.

11. The composition according to claim 1, wherein the biodegradable polymer comprises chitosan.

* * * * *